(12) United States Patent
Nakayama et al.

(10) Patent No.: US 10,758,427 B2
(45) Date of Patent: Sep. 1, 2020

(54) DISPOSABLE DIAPER

(71) Applicants: DAIO PAPER CORPORATION, Ehime (JP); NATIONAL UNIVERSITY CORPORATION TOTTORI UNIVERSITY, Tottori (JP)

(72) Inventors: Bin Nakayama, Tottori (JP); Yoshiko Suyama, Tottori (JP); Kaori Fujii, Tottori (JP); Nobutada Nishiura, Tottori (JP); Aya Ohshima, Tochigi (JP)

(73) Assignees: Daio Paper Corporation, Ehime (JP); National University Corporation Tottori University, Tottori (JP)

( * ) Notice: Subject to any disclaimer, the term of this patent is extended or adjusted under 35 U.S.C. 154(b) by 700 days.

(21) Appl. No.: 15/108,463

(22) PCT Filed: Dec. 26, 2014

(86) PCT No.: PCT/JP2014/084450
§ 371 (c)(1),
(2) Date: Jun. 27, 2016

(87) PCT Pub. No.: WO2015/099103
PCT Pub. Date: Jul. 2, 2015

(65) Prior Publication Data
US 2016/0317363 A1      Nov. 3, 2016

(30) Foreign Application Priority Data

Dec. 27, 2013   (JP) .................................. 2013-273417
May 19, 2014   (JP) .................................. 2014-103473
Jun. 19, 2014   (JP) .................................. 2014-126255

(51) Int. Cl.
*A61F 13/15*      (2006.01)
*A61F 13/20*      (2006.01)
(Continued)

(52) U.S. Cl.
CPC ........ *A61F 13/49* (2013.01); *A61F 13/49001* (2013.01); *A61F 13/49009* (2013.01); *A61F 13/532* (2013.01); *A61F 13/535* (2013.01)

(58) Field of Classification Search
CPC ................ A61F 13/49; A61F 13/49001; A61F 13/49009; A61F 13/532; A61F 13/49092;
(Continued)

(56) References Cited

U.S. PATENT DOCUMENTS 5,062,840 A * 11/1991 Holt ...................... A61F 13/495
                                                     604/385.19
5,462,541 A    10/1995 Bruemmer et al.
(Continued)

FOREIGN PATENT DOCUMENTS

JP      04-300543 A    10/1992
JP      2001-293034 A  10/2001
(Continued)

*Primary Examiner* — Michele M Kidwell
(74) *Attorney, Agent, or Firm* — Muncy, Geissler, Olds & Lowe, P.C.

(57) ABSTRACT

The present invention aims at providing a disposable diaper having excellent maintainability of a surface space and capable of being easily produced. It is characterized in that a lower layer absorbent body has, at least at center of a crotch portion in a width direction, an elongated lower layer through section piercing in a thickness direction and extending in a front-back direction; an upper layer absorbent body has an upper layer through section piercing in the thickness direction at least within a range corresponding to the lower layer through section in the front-back direction, the upper layer through section has an elongated middle section extending in the front-back direction so as to be located above the lower layer through section, and extending sections which extend, in the width direction, from both sides of a back side position of the middle section, and a side edge of the extending section has a shape in which at least a part
(Continued)

of the front side thereof is located further outside in the width direction toward the back side.

6 Claims, 29 Drawing Sheets

(51) Int. Cl.
  *A61F 13/49* (2006.01)
  *A61F 13/535* (2006.01)
  *A61F 13/532* (2006.01)
(58) Field of Classification Search
  CPC .......... A61F 13/49093; A61F 13/49088; A61F 13/535
  See application file for complete search history.

(56) References Cited

U.S. PATENT DOCUMENTS

| | | | | |
|---|---|---|---|---|
| 6,498,283 B1* | 12/2002 | Wada | ................. | A61F 13/4946 |
| | | | | 604/358 |
| 6,926,703 B2* | 8/2005 | Sugito | ............... | A61F 13/49406 |
| | | | | 604/378 |
| 7,666,175 B2* | 2/2010 | Trennepohl | ....... | A61F 13/49017 |
| | | | | 604/385.01 |
| 8,968,263 B2* | 3/2015 | Watabe | ............ | A61F 13/15699 |
| | | | | 604/385.101 |
| 9,119,749 B2* | 9/2015 | Close | ................ | A61F 13/49007 |
| 9,913,763 B2* | 3/2018 | Ryu | ................... | A61F 13/49001 |
| 2004/0243087 A1* | 12/2004 | Kinoshita | ........... | A61F 13/4753 |
| | | | | 604/385.04 |
| 2006/0069371 A1* | 3/2006 | Ohashi | ................ | A61F 13/4704 |
| | | | | 604/385.01 |
| 2007/0208319 A1 | 9/2007 | Minato | | |
| 2012/0220972 A1 | 8/2012 | Kawamura et al. | | |
| 2013/0231628 A1* | 9/2013 | Dieringer | .......... | A61F 13/47236 |
| | | | | 604/385.101 |

FOREIGN PATENT DOCUMENTS

| | | |
|---|---|---|
| JP | 2003-070842 A | 3/2003 |
| JP | 2004-024308 A | 1/2004 |
| JP | 2007-268253 A | 10/2007 |
| JP | 2010-187919 A | 9/2010 |
| JP | 2011-104021 A | 6/2011 |
| JP | 2011-125537 A | 6/2011 |
| JP | 2013-017531 A | 1/2013 |
| JP | 2013-135716 A | 7/2013 |
| JP | 2013-135717 A | 7/2013 |
| JP | 5-621067 B1 | 11/2014 |

* cited by examiner

DISPOSABLE DIAPER

TECHNICAL FIELD

The present invention relates to a disposable diaper having leakage prevention property.

BACKGROUND ART

There are many leakage modes in the disposable diaper, and one of them is leakage of urine from a ventral side when a wearer is a man (leakage from the ventral side of a disposable diaper, which may sometimes be referred to as "leakage from the ventral side in a man"). When the wearer is a woman, the leakage from the ventral side in a man does not occur, but when the wearer is a man, it occurs, even if other conditions are the same. The cause thereof is, as shown in Patent Documents 1 and 2, that a scrotum, located back to an excreted position of urine, adheres to a disposable diaper surface and a space between them becomes extremely small, whereby the backward movement of the urine is blocked.

According to the present inventors' later studies, it has been found that when a single amount of urine excreted is large, or even if the amount is small when the urine is excreted multiple times, regardless of sex, the absorption of the urine is too late to be effective, and a traveling time of the urine on the disposable diaper surface is long, but because of the small space between a surface of a crotch portion of the disposable diaper and a surface of the body (hereinafter which may sometimes be referred to as a "surface space"), it is difficult to diffuse the urine backward and the urine tends to be easily leaked from part around the groins at which space is easily formed.

CITATION LIST

Patent Documents
  Patent Document 1: JP-A No. 2013-135716
  Patent Document 2: JP-A No. 2013-135717
  Patent Document 3: JP-A No. 2011-104021
  Patent Document 4: JP-A No. 2011-125537

SUMMARY OF INVENTION

Technical Problem

As a means of solving the leakage caused by such small surface space, proposals described in Patent Documents 1 and 2, filed by the same applicants as the present applicant, are effective regardless of sex, but there is room for improvement in an invention described in Patent Document 1 in terms of shape-maintaining property of depression forming the surface space, or in an invention described in Patent Document 2 in terms of production easiness.

The main object of the present invention is to provide a disposable diaper having the excellent maintaining property of a surface space and capable of being easily produced.

Solution to Problem

The present inventions solving the problems described above are as follows:
<Invention of Claim 1>
A disposable diaper comprising a crotch portion, a back side part extending backward from the crotch portion, and an absorbent body extending from the crotch portion to the back side part for absorbing urine, wherein
  the absorbent body has, at least at center of the crotch portion in a width direction, an area for forming surface depression formed of at least one of a through section piercing in a thickness direction and a thin section,
  the area for forming surface depression has an elongated first depression-formed part extending in a front-back direction, and second depression-formed parts extending in the width direction from both sides of an intermediate position or a back side position of the first depression-formed part in the front-back direction, and
  the second depression-formed part is the thin section, and the first depression-formed part is the through section piercing in the thickness direction or a part which is thinner than the second depression-formed part.
(Operation and Effect)
  According to the present invention, when the disposable diaper is put between both legs and compressed in a width direction in a wearing state, a depression is formed on the diaper surface as the area for forming surface depression is deformed outward in order from the center in the width direction so as to be pushed out from the diaper. At that time, in the area for forming surface depression, an area of the first depression-formed part and the second depression-formed parts is wider than an area of only the first depression-formed part by the width of the second depression-formed parts, and thus a depression part formed in the former area is wider than that in the latter area. Moreover, the stiffness of the wider depression part is secured to a certain degree by the thin section, and thus maintainability of the shape and the depth of the depression, and further maintainability of the surface space become excellent. When urine is excreted, urine excreted in the depression area and its front side, which is not absorbed and moves on the diaper surface, flows backward in the large surface space as a passage, during which the urine is absorbed in the absorbent body located on the back side. A conventional problem of diffusion block caused by the small surface space, accordingly, can be effectively prevented. It has been known to improve the diffusibility in a front-back direction by providing slits in the front-back direction on the absorbent body, but the present invention has effects far from those of the well-known technique of improving the diffusion described above.
<Invention According to Claim 2>
  The disposable diaper according to claim 1, wherein the absorbent body has a monolayer structure.
(Operation and Effect)
  Even if the absorbent body has the monolayer structure, the effects described above can be obtained by providing the area for forming surface depression of the present invention.
<Invention According to Claim 3>
  The disposable diaper according to claim 1, wherein the absorbent body is a stack of multiple absorbent body layers.
(Operation and Effect)
  Even if the absorbent body has the multi-layer structure, the effects described above can be obtained by providing the area for forming surface depression of the present invention.
<Invention According to Claim 4>
  A disposable diaper comprising a crotch portion, a back side part extending backward from the crotch portion, and an absorbent body extending from the crotch portion to the back side part for absorbing urine, wherein
  the absorbent body contains a lower layer absorbent body and an upper layer absorbent body provided on the lower layer absorbent body, the lower layer absorbent body has, at least at center of the crotch portion in a width direction, an elongated lower layer through section piercing in a thickness direction and extending in a front-back direction, the upper layer absorbent body has an upper layer through section piercing in the thickness direction at least within a range corresponding to the lower layer through section in the front-back direction, and the upper layer through section has an elongated middle section extending in the front-back direction so as to be located above the lower layer through section, and extending sections extending in the width direction, from both sides of an intermediate position or a back side position of the middle section in the front-back direction.

(Operation and Effect)

The invention according to this claim relates to an application in which the absorbent body has a two-layer structure. In the absorbent body having the two-layer structure as described in this claim, there is no absorbent body at the overlapped part of the lower layer through section and the middle section of the upper layer through section, the site of extending section of the upper layer through section has a monolayer structure of the lower layer absorbent body, and the outside of the extending section of the upper layer through section has the two-layer structure of the upper layer absorbent body and the lower layer absorbent body. When the disposable diaper is put between both legs and compressed in a width direction in a wearing state, edges of both sides of each through section approach each other according to the compression amount, because there is no absorbent body at the overlapped part of the lower layer through section and the middle section of the upper layer through section. At that time, though forces are also applied to the monolayer structures, which are located on both the extending sections of the upper layer through section, in a direction approaching each other, the monolayer structure parts are folded to the underside toward the two-layer structure parts of the outside thereof in the width direction, because the monolayer structure parts are easily folded to the underside along side edges of the extending sections of the upper layer through section, which are boundaries with the two-layer structure parts, and no absorbent body-part between the both monolayer structure parts subsides toward the underside, whereby a wide depression is formed on the disposable diaper surface.

Such depression can be easily restored to the compression in the width direction, not only that but the depth of the depression can be maintained because the monolayer structure part, folded to the underside, serves as a wall, and thus the maintainability of the depression and further the maintainability of the surface space are excellent. Also in the invention according to this claim, when urine is excreted, urine excreted in the front side of the depression area, which is not absorbed and moves on the diaper surface, flows backward in the large surface space as a passage, during which the urine is absorbed in the absorbent body located on the back side. The conventional problem of diffusion block caused by the small surface space, accordingly, can be effectively prevented. It has been known to improve the diffusibility in a front-back direction by providing slits in the front-back direction on the absorbent body, but the present invention has effects far from those of the well-known technique of improving the diffusion described above.

In addition, it is established as the production technique to form the absorbent body as a two-layer structure and to provide the through section in the thickness direction in each layer, and thus productions can be easily performed only changing the shapes or the positional relations.

<Invention According to Claim 5>

The disposable diaper according to claim 4, wherein the middle section of the upper layer through section extends up to a front end of the upper layer absorbent body, and opens at the front end of the upper layer absorbent body, and the front end of the upper layer absorbent body is located at a same position as or a back side position of a front end of the lower layer through section.

(Operation and Effect)

It is preferable that the upper layer through section extends to reach the front end of the upper layer absorbent body and the front end of the upper layer absorbent body is located at the same position as or the back side position of the front end of the lower layer absorbent body. By doing so, when the crotch portion is compressed in the width direction, higher compression is likely to be applied toward the front side of the upper layer absorbent body and further the front side of the upper layer through section. Thus, the depression described above can be easily formed.

<Invention According to Claim 6>

The disposable diaper according to claim 4 or 5, wherein the lower layer through section is provided at an intermediate position of the lower layer absorbent body in the front-back direction.

(Operation and Effect)

When the lower layer through section is disposed so that it does not extend to reach the front and back ends of the lower layer absorbent body, the stiffness of the absorbent body can be secured as a whole.

<Invention According to Claim 7>

The disposable diaper according to any one of claims 4 to 6, which contains a diffusion sheet, which promotes urine diffusion in the front-back direction, on a bottom of the lower layer through section.

(Operation and Effect)

When such diffusion sheet is provided, the diffusion of urine passing through the lower layer through section in the front-back direction can be promoted.

<Invention According to Claim 8>

A disposable diaper comprising a crotch portion, a back side part extending backward from the crotch portion, and an absorbent body extending from the crotch portion to the back side part for absorbing urine, wherein the absorbent body contains a lower layer absorbent body and an upper layer absorbent body provided on the lower layer absorbent body, the lower layer absorbent body has, at least at center of the crotch portion in a width direction, an elongated lower layer thin section extending in a front-back direction, the upper layer absorbent body has an upper layer through section piercing in a thickness direction at least within a range corresponding to the lower layer thin section in the front-back direction, and the upper layer through section has an elongated middle section extending in the front-back direction so as to be located above the lower layer thin section, and extending sections extending in the width direction from both sides of an intermediate position or a back side position of the middle section in the front-back direction.

(Operation and Effect)

Even if the thin section is adopted instead of the through section in the lower layer absorbent body in the invention according to claim 4, as described in this claim, the same advantages as above can be obtained. In the absorbent body having the two-layer structure as described in this claim, the overlapped part of the lower layer thin section and the middle section of the upper layer through section, there is the monolayer structure of the lower layer thin section, the site of the extending section of the upper layer through section has the monolayer structure of the lower layer absorbent body excluding the thin section, and the outside of the extending section of the upper layer through section has the two-layer structure of the upper layer absorbent body and the lower layer absorbent body. When the disposable diaper is put between both legs and compressed in a width direction in a wearing state, though forces are applied to the monolayer structure parts located on the extending sections of the upper layer through section in a direction approaching each other, the monolayer structure parts are folded to the underside toward the two-layer structure parts of the outside thereof in the width direction, because the monolayer structure parts are easily folded to the underside along side edges of the extending sections of the upper layer through section, which are boundaries with the two-layer structure parts, and a part between the monolayer structure parts subsides toward the underside, whereby a wide depression is formed on the disposable diaper surface.

Such depression can be easily restored to the compression in the width direction, not only that but the depth of the depression can be maintained because the monolayer structure part, folded to the underside, serves as a wall, and thus the maintainability of the depression and further the maintainability of the surface space are excellent. Also in the invention according to this claim, when urine is excreted, urine excreted in the front side of the depression area, which is not absorbed and moves on the diaper surface, flows backward in the large surface space as a passage, during which the urine is absorbed in the absorbent body located on the back side. The conventional problem of diffusion block caused by the small surface space, accordingly, can be effectively prevented. It has been known to improve the diffusibility in a front-back direction by providing slits in the front-back direction on the absorbent body, but the present invention has effects far from those of the well-known technique of improving the diffusion described above.

In addition, it is established as the production technique to form the absorbent body as the two-layer structure and to provide the through section in the thickness direction in each layer, and thus easy productions can be performed only changing the shapes or the positional relations.

<Invention According to Claim 9>

The disposable diaper according to claim 8, wherein the middle section of the upper layer through section extends up to a front end of the upper layer absorbent body and opens at the front end of the upper layer absorbent body, and the front end of the upper layer absorbent body is located at a same position as or a back side position of a front end of the lower layer thin section.

(Operation and Effect)

It is preferable that the upper layer through section extends to reach the front end of the upper layer absorbent body and the front end of the upper layer absorbent body is located at the same position as or the back side position of the front end of the lower layer absorbent body. By doing so, higher compression is likely to be applied toward the front side of the upper layer absorbent body and further the front side of the upper layer through section when the crotch portion is compressed in the width direction. Thus, the depression described above can be easily formed.

<Invention According to Claim 10>

The disposable diaper according to claim 8 or 9, wherein the lower layer thin section is provided at an intermediate position of the lower layer absorbent body in the front-back direction.

(Operation and Effect)

When the lower layer thin section is disposed so that it does not extend to reach the front and back ends of the lower layer absorbent body, the stiffness of the absorbent body can be secured as a whole.

<Invention According to Claim 11>

The disposable diaper according to any one of claims 4 to 10, wherein three-dimensional gathers at the crotch portion extend at both sides of a diaper surface in the width direction, the three-dimensional gather has a projecting portion, which projects from a lateral side of the upper layer through section and which extends in the front-back direction, the projecting portion contains non-standing parts, which are fixed in a fallen state and which are positioned in a front side and in a back side of the projecting portion respectively, and a standing part, which is not fixed, which is disposed between the non-standing parts, and which has a resilient and elastic gather member fixed in a stretched state in the front-back direction, and the extending section is located between the non-standing parts of the three-dimensional gather at the crotch portion in the front-back direction.

(Operation and Effect)

By the presence of such three-dimensional gather at the crotch portion, a contracting force owing to the resilient and elastic gather member on the three-dimensional gather at the crotch portion acts more effectively on the monolayer structure part, the formation of the depression is promoted, and the shape-maintaining property of the depression is improved. In addition, the monolayer structure parts, located on the extending sections of the upper layer through section, serve as the walls of the depression, and in these parts including the part between them, absorptivity of the absorbent body is decreased so that the urine easily moves there, and thus what is called side leakage can be prevented by providing the three-dimensional gathers at the crotch portion at the both sides thereof.

<Invention According to Claim 12>

A disposable diaper comprising a crotch portion, a back side part extending backward from the crotch portion, and an absorbent body extending from the crotch portion to the back side part for absorbing urine, wherein the absorbent body contains an upper layer absorbent body and a lower layer absorbent body provided under the upper layer absorbent body, the upper layer absorbent body has, at least at center of the crotch portion in a width direction, an elongated upper layer through section piercing in a thickness direction or upper layer thin section extending in a front-back direction, the lower layer absorbent body has a lower layer through section piercing in the thickness direction at least within a range corresponding to the upper layer through section or upper layer thin section in the front-back direction, and the lower layer through section has an elongated middle section extending in the front-back direction so as to be located under the upper layer through section or upper layer thin section, and extending sections extending in the width direction from both sides of an intermediate position or a back side position of the middle section in the front-back direction.

(Operation and Effect)

Even if the shapes of the upper layer through section and the lower layer through section described in claim 4 and the shapes of the upper layer through section and the lower layer thin section described in claim 7 are upside down, as described in this claim, the same advantages as above can be obtained. In the absorbent body having the two-layer structure as described in this claim, there is no absorbent body or a monolayer structure of the upper layer thin section in the overlapped part of the upper layer through section or the upper layer thin section and the middle section of the lower layer through section, the site of the extending section of the lower layer through section has the monolayer structure of the upper layer absorbent body or the monolayer structure of the upper layer absorbent body excluding the thin section, and the outside of the extending section of the lower layer through section has the two-layer structure of the lower layer absorbent body and the upper layer absorbent body. When the disposable diaper is put between both legs and compressed in a width direction in a wearing state, though forces are applied to the monolayer structure parts located on the extending sections of the lower layer through section in a direction approaching each other, the monolayer structure parts are folded to the underside toward the two-layer structure parts of the outside thereof in the width direction, because the monolayer structure parts are easily folded to the underside along side edges of the extending sections of the lower layer through section, which are boundaries with the two-layer structure parts, and a part between both the monolayer structure parts subsides toward the underside, whereby a wide depression is formed on the disposable diaper surface.

Such depression can be easily restored to the compression in the width direction, not only that but the depth of the depression can be maintained because the monolayer structure part, folded to the underside, serves as a wall, and thus the maintainability of the depression and further the maintainability of the surface space are excellent. Also in the invention according to this claim, when urine is excreted, urine excreted in the front side of the depression area, which is not absorbed and moves on the diaper surface, flows backward in the large surface space as a passage, during which the urine is absorbed in the absorbent body located on the back side. The conventional problem of diffusion block caused by the small surface space, accordingly, can be effectively prevented. It has been known to improve the diffusibility in a front-back direction by providing slits in the front-back direction on the absorbent body, but the present invention has effects far from those of the well-known technique of improving the diffusion described above.

In addition, it is established as the production technique to form the absorbent body as the two-layer structure and to provide the through section in the thickness direction in each layer, and thus easy productions can be performed only changing the shapes or the positional relations.

<Invention According to Claim 13>

The disposable diaper according to claim 12, wherein three-dimensional gathers at the crotch portion extend at both sides of a diaper surface in the width direction, the three-dimensional gather has a projecting portion, which projects from a lateral side of the lower layer through section and which extends in the front-back direction, the projecting portion contains non-standing parts, which are fixed in a fallen state and which are positioned in a front side and in a back side of the projecting portion respectively, and a standing part, which is not fixed, which is disposed between the non-standing parts, and which has a resilient and elastic gather member fixed in a stretched state in the front-back direction, and the extending section is located between the non-standing parts of the three-dimensional gather at the crotch portion in the front-back direction.

(Operation and Effect)

By the presence of the three-dimensional gather at the crotch portion, a contracting force owing to the resilient and elastic gather member on the three-dimensional gather at the crotch portion acts more effectively on the monolayer structure parts, the formation of the depression is promoted, and the shape-maintaining property of the depression is improved. In addition, the monolayer structure parts, located on the extending sections of the lower layer through section, serve as walls of the depression, and, in these parts including parts between them, the absorption amount is small in the absorbent body so that the urine would easily move there, and thus what is called side leakage can be prevented by providing the three-dimensional gathers at the crotch portion at the both sides thereof.

<Invention According to Claim 14>

The disposable diaper according to claim 12 or 13, wherein the middle section of the lower layer through section extends up to a front end of the lower layer absorbent body and opens at the front end of the lower layer absorbent body, and the front end of the lower layer absorbent body is located at a same position as or a back side position of a front end of the upper layer through section or the upper layer thin section.

(Operation and Effect)

It is preferable that the lower layer through section extends to reach the front end of the lower layer absorbent body and the front end of the lower layer absorbent body is located at the same position as or the back side position of the front end of the upper layer absorbent body. By doing so, when the crotch portion is compressed in the width direction, higher compression is likely to be applied toward the front side of the upper layer absorbent body and further the front side of the upper layer through section. Thus, the depression described above can be formed easily.

<Invention According to Claim 15>

The disposable diaper according to any one of claims 12 to 14, wherein the upper layer through section is provided at an intermediate position of the upper layer absorbent body in the front-back direction.

(Operation and Effect)

When the upper layer through section is disposed so that it does not extend to reach the front and back ends of the upper layer absorbent body, the stiffness of the absorbent body can be secured as a whole.

<Invention According to Claim 16>

The disposable diaper according to any one of claims 4 to 15, wherein a side edge of the extending section has a shape in which at least a part of the front side thereof is located further outside in the width direction toward the back side.

(Operation and Effect)

It is preferable that the side edge of the extending section has the shape in which at least a part of the front side thereof is located further outside in the width direction toward the back side, (i.e., the right side edge is in a diagonally backward right direction, and the left side edge is in a diagonally backward left direction). By doing so, the width of the monolayer structure part located in the extending section is gradually increased toward the back side, and thus the monolayer structure part is gradually folded to the underside toward the two-layer structure part outside in the width direction toward the back side. At that time, a part having no absorbent body between the monolayer structure parts subsides toward the underside, whereby an almost boat-shaped depression is formed on the disposable diaper surface. Such boat-shaped depression can be easily restored to the compression in the width direction, not only that but the depth of the depression can be maintained because the monolayer structure part, folded to the underside, serves as a wall, and thus the maintainability of the boat-shaped depression and further the maintainability of the surface space are excellent.

<Invention According to Claim 17>

The disposable diaper according to any one of claims 4 to 16, wherein the extending section has a trapezoid shape whose base line is a boundary with the middle section.

(Operation and Effect)

When the extending sections have the shape described above, the production is preferably easy.

Effects of the Invention

As described above, the present invention provides the advantages including the excellent maintainability of the surface space, easy production, and the like.

DESCRIPTION OF EMBODIMENTS

Figure 1:
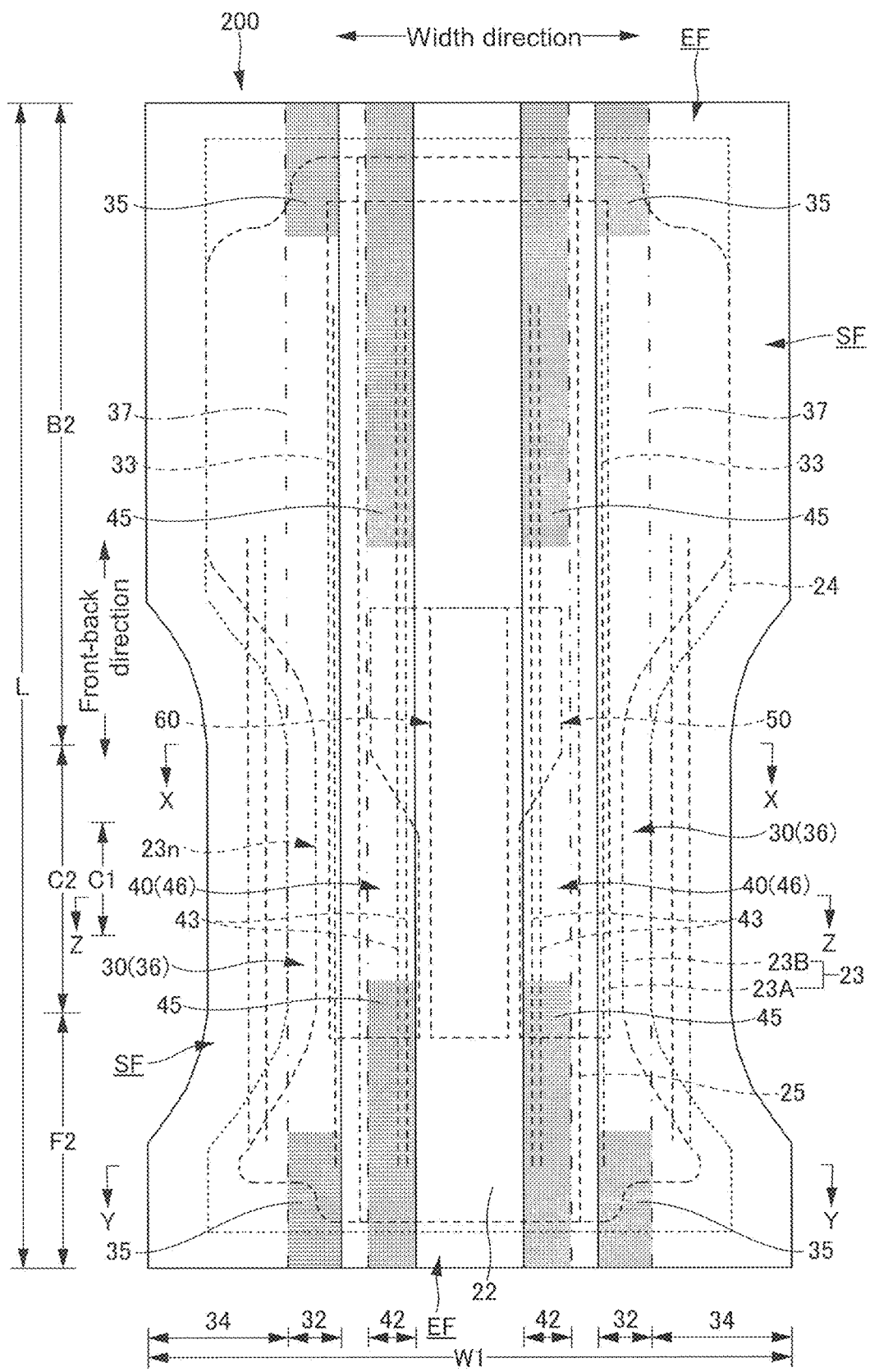
FIG. 1 is a plan view showing an inner-surface side of a pad-type disposable diaper in a developed state.
Figure 2C:
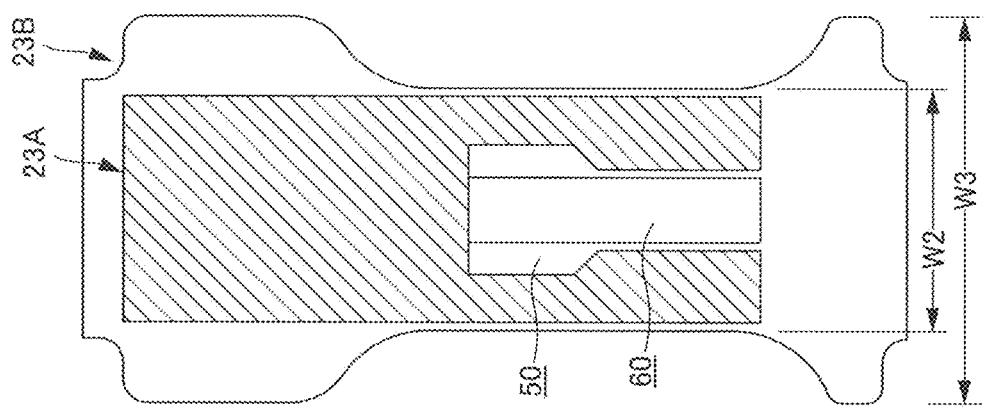
FIGS. 2(a) to (c) are plan views showing, respectively, (a) a lower layer absorbent body, (b) an upper layer absorbent body, and (c) a laminated state of the lower layer absorbent body and the upper layer absorbent body.
Figure 2B:
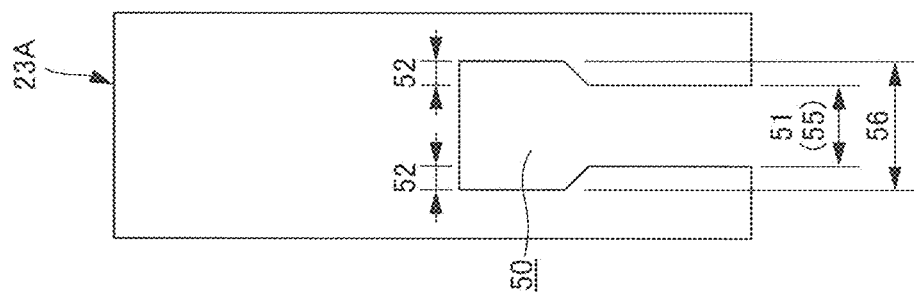
Figure 2A:
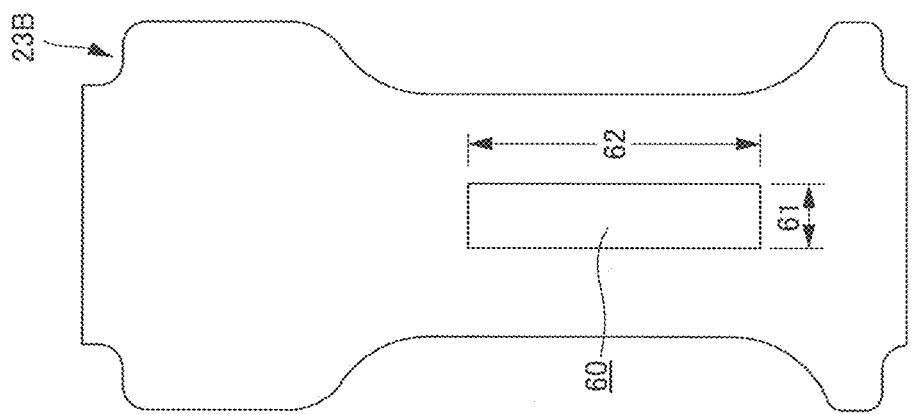
Figure 3:
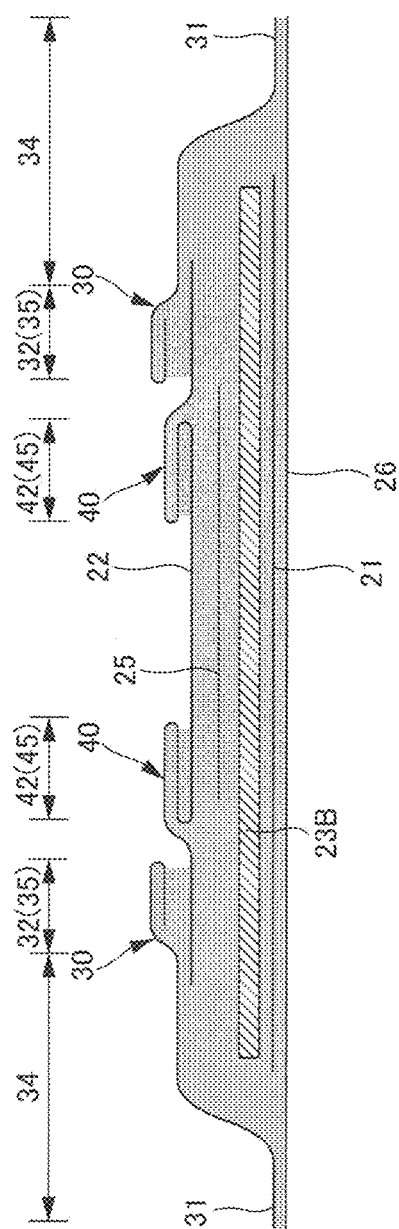
FIG. 3 is a cross-sectional view at Y-Y of FIG. 1.
Figure 4A:
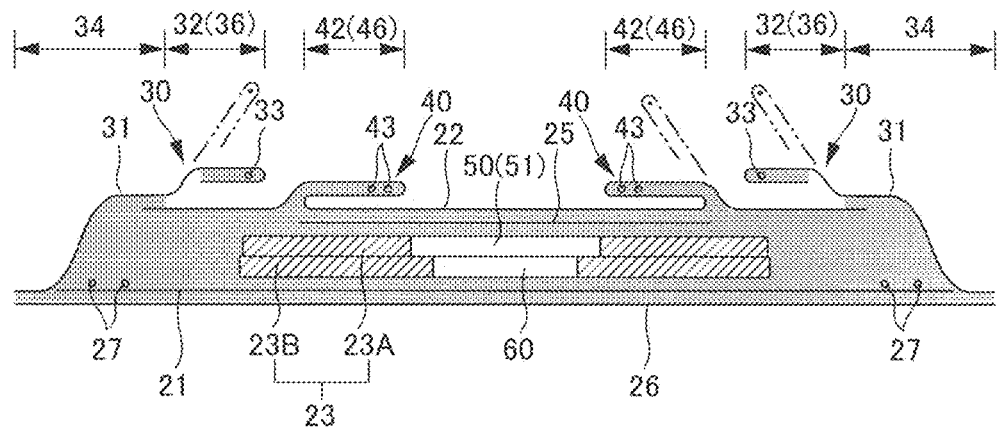
FIG. 4(a) is a Z-Z cross-sectional view in FIG. 1
Figure 4B:
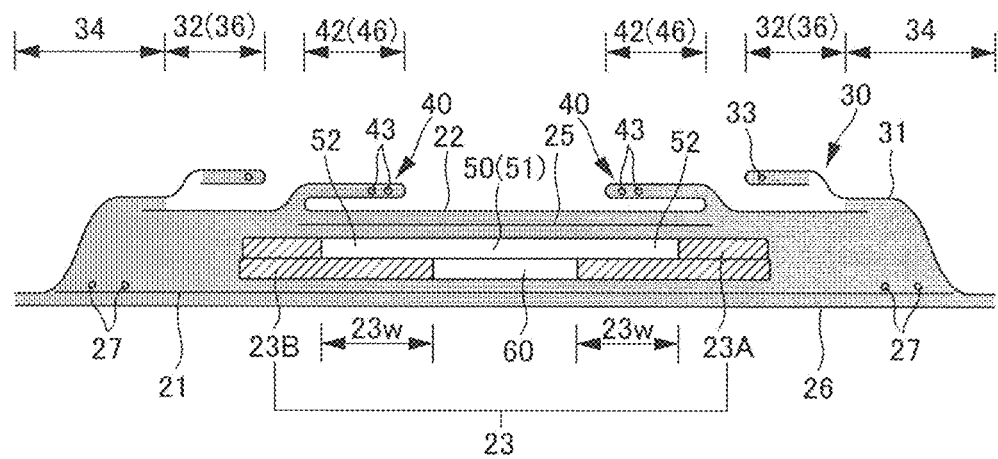
FIG. 4(b) is an X-X cross-sectional view in FIG. 1.
Figure 5:
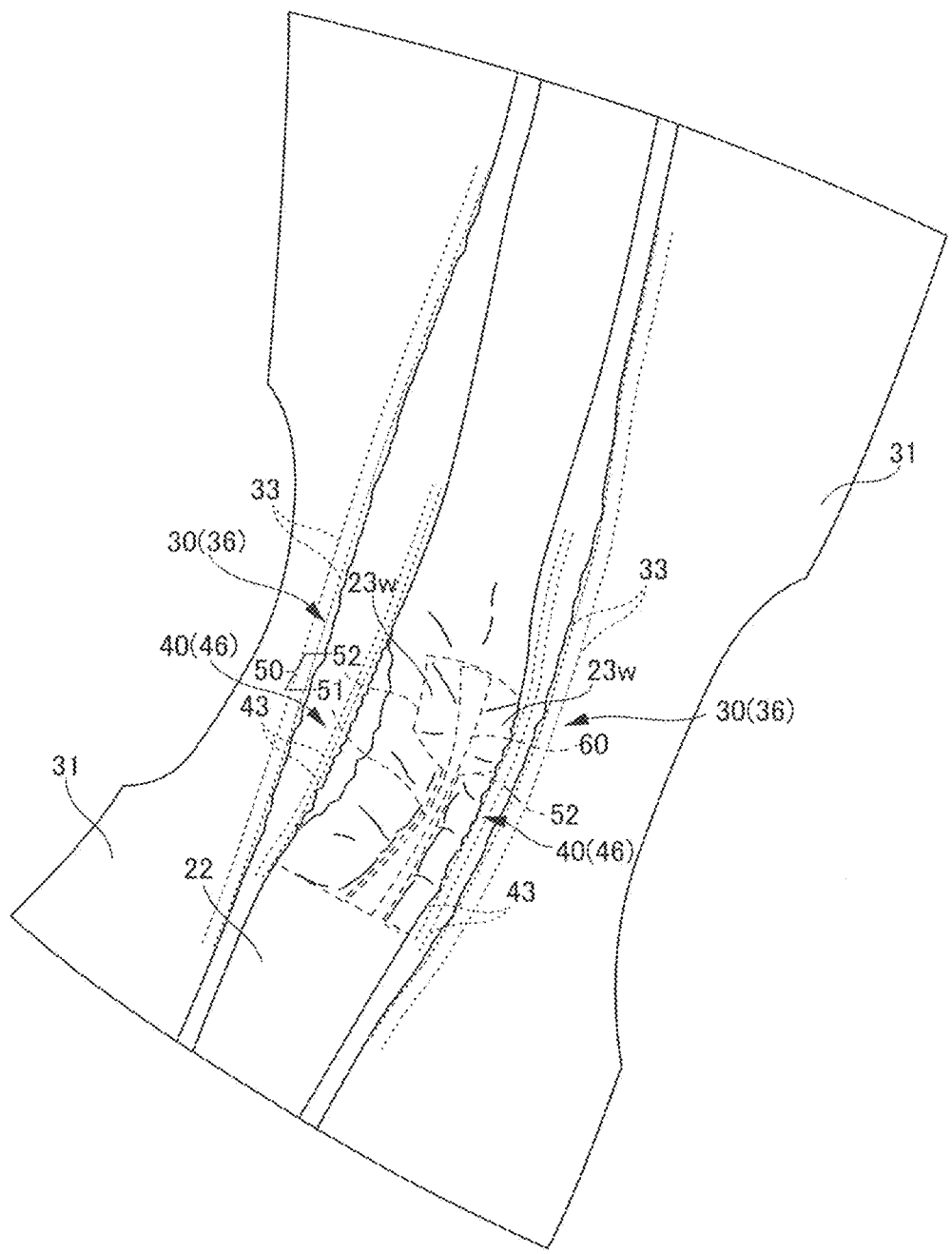
FIG. 5 is a perspective view.

One embodiment of the present invention is explained in detailed below, referring to an example of a pad-type disposable diaper shown in the drawings attached.

FIG. 1 to FIG. 6 show a pad-type disposable diaper 200. The pad-type disposable diaper 200 has a crotch portion C2, and a front side part F2 and a back side part B2 which extend forward and backward. A size of each part can be appropriated decided. For example, a full length L (a length in a front-back direction) of a diaper may be adjusted to about 350 to 700 mm, and a whole width W1 of the diaper may be adjusted to about 130 to 400 mm. In that case, a length of a crotch portion C2 in the front-back direction may be adjusted to about 10 to 150 mm, a length of a front side part F2 in the front-back direction may be adjusted to about 50 to 350 mm, and a length of a back side part B2 in the front-back direction may be adjusted to about 50 to 350 mm. The "crotch portion" refers to a part facing a crotch of the body when the diaper is used, which may be a range of the center or the vicinity thereof to a predetermined site in a front side of an article in a front-back direction as in embodiments shown in the drawings, or a predetermined range at the center of an article in a front-back direction, depending on the product. When there is a narrower part with small width at the middle of the article in the front-back direction or at the middle of the absorbent body in the front-back direction as shown in the drawing, the "crotch portion" refers to a predetermined range in the front-back direction wherein the site of the narrower part with the minimum width is the center of the front-back direction. The "front side part (a ventral side part)" refers to a part in front of the crotch portion, and the "back side part (a dorsal side part)" refers to a part in back side of the crotch portion.

The pad-type disposable diaper 200 has a basic structure in which an absorbent body 23 is put between a liquid-impermeable sheet 21 and a liquid-permeable top sheet 22. Parts depicted by dot patterns in the drawing show joined parts at which structural members are joined, which are formed by solid, bead, curtain, summit, or spiral coating with a hot melt adhesive, or the like.

(Liquid-Impermeable Sheet • Outer Sheet)

The liquid-impermeable sheet 21 is provided on the underside of the absorbent body 23 so that the sheet is projected a little from a periphery of the absorbent body 23. As the liquid-impermeable sheet 21, sheets having moisture permeability without impairing water barrier property can be used in terms of the prevention of stuffiness, in addition to polyethylene films and the like. As the water barrier • moisture permeability sheet, for example, microporous sheets can be used which are obtained by melt-kneading an olefin resin such as polyethylene or polypropylene with an inorganic filler to form into a sheet, and then monoaxially or biaxially stretching it.

An outer surface of the liquid-impermeable sheet 21 may be covered with an outer sheet 26 formed of a non-woven fabric. In that case, the liquid-impermeable sheet 21 may have a width almost the same as the width of the absorbent body 23. Various non-woven fabrics may be used for the outer sheet 26. As a fiber material, forming the non-woven fabric, regenerated fibers such as rayon and cupra and natural fibers such as cotton may be used, in addition to synthetic fibers including olefin fibers such as polyethylene and polypropylene, polyester fibers, amide fibers and the like.

(Liquid-Permeable Top Sheet)

The top face of the absorbent body 23 is covered with the liquid-permeable top sheet 22. In the embodiments shown in the drawings, the absorbent body 23 is partly projected from the side edge of the top sheet 22, but the width of the top sheet 22 may be widened so that the side edge of the absorbent body 23 is not projected therefrom. As the top sheet 22, non-woven fabrics with or without holes or perforated plastic sheets are used. As a fiber material forming the non-woven fabric, regenerated fibers such as rayon and cupra and natural fibers such as cotton may be used, in addition to synthetic fibers including olefin fibers such as polyethylene and polypropylene, polyester fibers, amide fibers and the like.

It is desirable that an interlayer sheet 25 is put between the top sheet 22 and the absorbent body 23. The interlayer sheet 25 is provided in order to prevent the return of urine absorbed in the absorbent body 23, and it is desirable to use a material having a low water-holding property and a high liquid permeability, for example, a non-woven fabric or a mesh film. When a front end of the top sheet 22 is assumed to be 0% and a back end of the top sheet 22 is assumed to be 100%, it is preferable that a front end of the interlayer sheet 25 is located in a range of 0 to 11%, and a back end of the interlayer sheet 25 is located in a range of 92 to 100%. The interlayer sheet 25 preferably has a width 25w of about 50 to 90% the width W2 of the absorbent body 23.

(End Flap Part and Side Flap Part)

At both ends of the pad-type disposable diaper 200 in the front-back direction, the outer sheet 26 and the liquid-permeable top sheet 22 extend forward and backward from the front and back ends of the absorbent body 23 and they are bonded together, whereby end flap parts EF having no absorbent body 23 are formed. At both sides of the pad-type disposable diaper 200, the outer sheet 26 extends outward from the both side edges of the absorbent body 23, and an outer part 34 of a three-dimensional gather sheet 31 at the side part in the width direction is bonded entirely in the front-back direction to the inside of a part from the extending part to the side part of the top sheet 22, whereby side flap parts SF having no absorbent body 23 are formed. The bonded parts can be formed using a hot melt adhesive, heat-sealing, or ultrasonic sealing. When the outer sheet 26 is not provided, the liquid-impermeable sheet 21, instead of the outer sheet 26, extends up to the side flap part SF, whereby the outer surface of the side flap part SF can be formed.

(Three-Dimensional Gather at Side Part)

At both sides of a top face, three-dimensional gathers 30 at the side part, which extend in the front-back direction, are provided. The three-dimensional gather 30 at the side part is formed by the three-dimensional gather sheet 31 at the side part described above. A center part 32 of the three-dimensional gather sheet 31 at the side part in the width direction extends above the top sheet 22, and a resilient elastic member 33 for the three-dimensional gather at the side part is fixed to the end of the center part in the width direction along the front-back direction in the stretched state with a hot melt adhesive, or the like.

As a material for the three-dimensional gather sheet 31 at the side part, plastic sheets and melt-blown non-woven fabrics may be used, and non-woven fabrics which are subjected to a water repellent treatment with silicone, or the like, are preferably used in terms of the feel of the skin. As the resilient elastic member 33 for the three-dimensional gather at the side part, usually used materials may be used, which include styrene rubber, olefin rubber, urethane rubber, ester rubber, polyurethane, polyethylene, polystyrene, styrene-butadiene, silicone, and polyester, which are formed into an elongated state such as a thread, a string, or band. Each plane resilient and elastic gather member 7 has preferably a stretch rate during fixing of about 170 to 200%. The term "stretch rate" is a value when a natural length is assumed to be 100%.

In the three-dimensional gather sheet 31 at the side part, the outer part 34 in the width direction is bonded entirely in the front-back direction to the inside of the diaper (in the embodiment shown in the drawing, a top face of the top sheet 22 and the inside of the outer sheet 26) to form a fixed part 34 and, at the same time, the center part 32 in the width direction extends from the fixed part to form a projecting portion 32. Both ends of the projecting portion 32 in the front-back direction are bonded to the top face of the diaper (in the embodiment shown in the drawing, the top face of the top sheet 22) in the fallen state to form non-standing parts 35 and, at the same time, a part between the non-standing parts 35 is not fixed to the top face of the diaper (in the embodiment shown in the drawing, the top face of the top sheet 22) to form a standing part 36. The standing part 36 is a part which stands from the top face of the diaper (in the embodiment shown in the drawing, the top face of the top sheet 22), as shown by two-dot chain lines in FIG. 4, by applying a contracting force owing to the resilient elastic member 33 for the three-dimensional gather at the side part, and is brought into contact with an inguinal region, and a standing base end 37 thereof is located at a boundary of the fixed part 34 and the projecting portion 32 in the three-dimensional gather sheet 31 at the side part.

(Plane Gathers)

In the middle part of the side flap part SF in the front-back direction, elongated plane resilient and elastic gather members 27 are fixed in the front-back direction in the stretched state with a hot melt adhesive between the three-dimensional gather sheet 31 at the side part and the liquid-impermeable sheet 21 (the members may be located between the liquid-impermeable sheet 21 and the outer sheet 26), and what is called plane gathers are formed by the contracting of the plane resilient elastic gather members 27 in the side flap part SF. The side parts of the diaper are elastically resilient by the plane gathers for confirming to a region around the legs.

The number of plane resilient and elastic gather member 27 can be appropriately decided at each side of right and left, and about 1 to 10 members are preferable and about 2 to 5 members are more preferable. When multiple members are used, the space between two members is preferably from about 2 to 15 mm, particularly preferably from about 6 to 10 mm. As the plane resilient and elastic gather member 27, usually used materials may be used, which include styrene rubber, olefin rubber, urethane rubber, ester rubber, polyurethane, polyethylene, polystyrene, styrene-butadiene, silicone, and polyester, which are formed into a long and narrow state such as a thread, a string, or band. The fineness thereof is from about 500 to 1500 dtex, and in the natural rubber, the thickness is preferably from about 0.1 to 3 mm, particularly preferably from about 0.5 to 3 mm. Each plane resilient and elastic gather member 27 has preferably a stretch rate during fixing of about 150 to 250%.

(Absorbent Body)

The absorbent body 23 has a two-layer structure of a lower layer absorbent body 23B and an upper layer absorbent body 23A provided on the lower layer absorbent body 23B.

Figure 7:
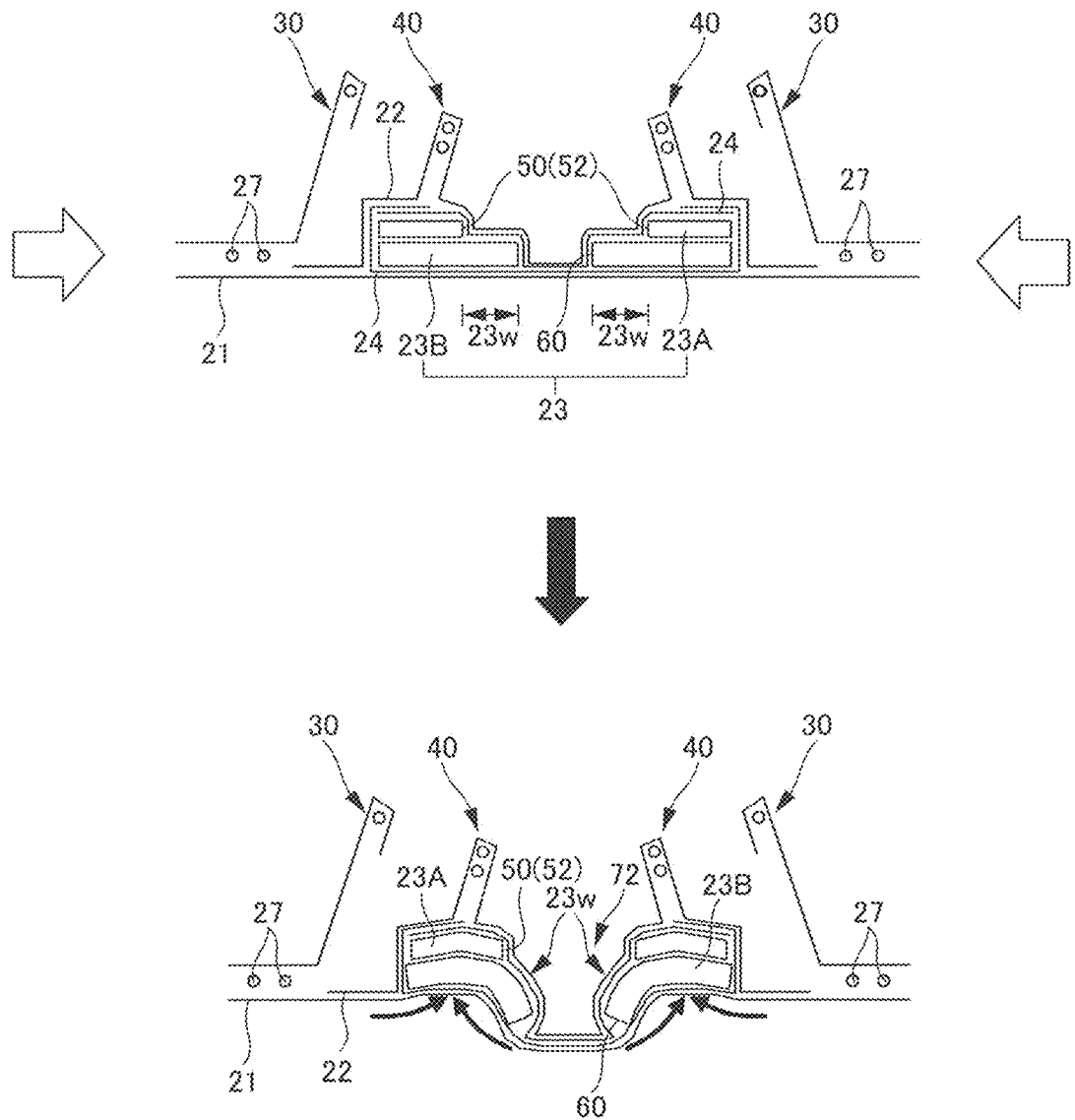
FIG. 7 is a schematic cross-sectional view showing change of a state before and after wearing.
Figure 9:
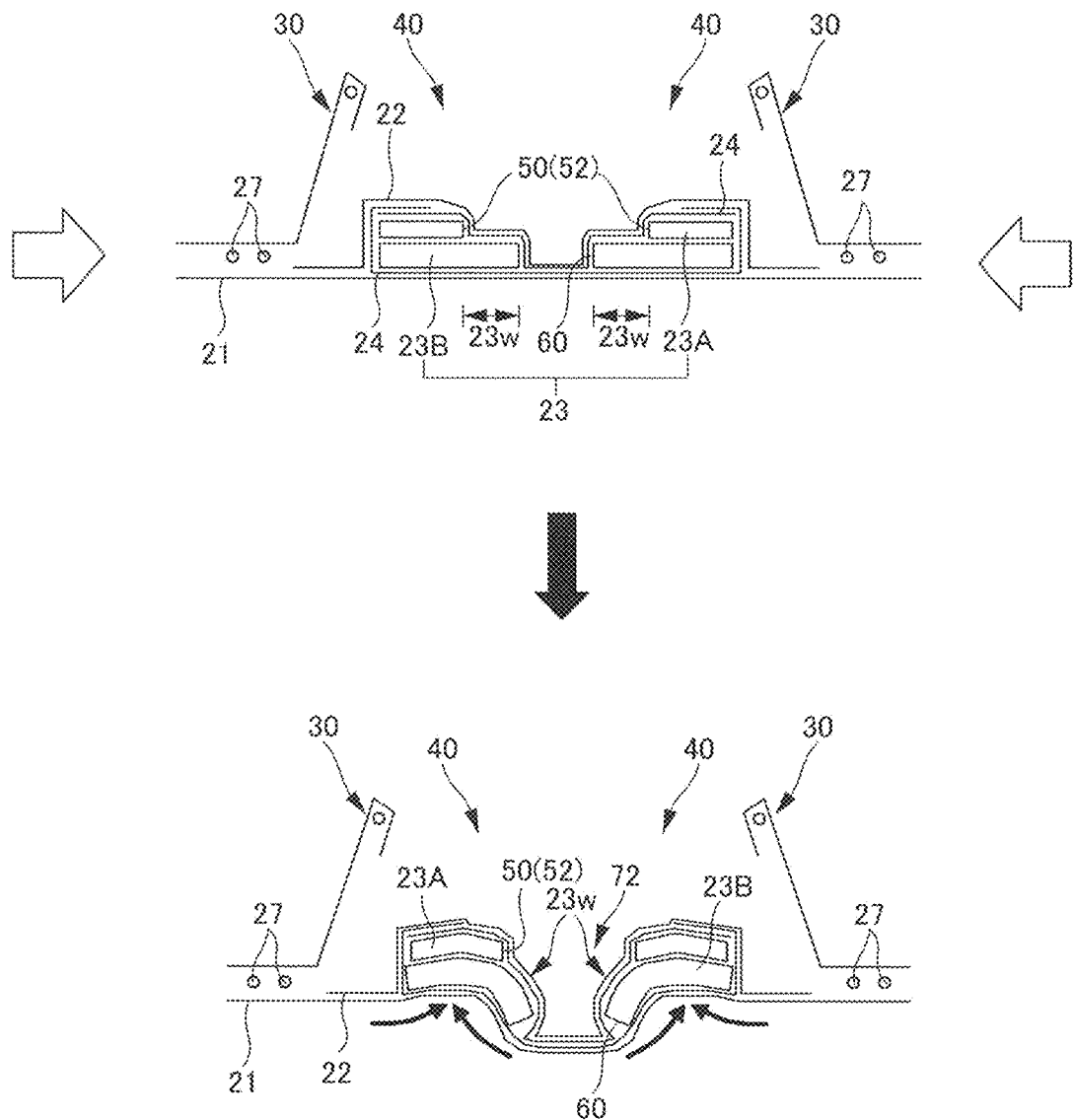
FIG. 9 is a schematic cross-sectional view showing change of a state before and after wearing.

As the lower layer absorbent body 23B and the upper layer absorbent body 23A, a material may be used, which is formed of a fiber accumulated body of pulp fibers, a filament assembly of, for example, cellulose acetate, or a non-woven fabric-based article with which high absorbent polymer particles are mixed or to which the polymer particles are adhered if necessary. The fiber basis weight of the lower layer absorbent body 23B and the upper layer absorbent body 23A, and the basis weight of the high absorbent polymer may be appropriately decided, and the fiber basis weight is preferably adjusted to about 140 to 230 g/m$^2$, and the basis weight of the high absorbent polymer is preferably adjusted to about 60 to 90 g/m$^2$. When the high absorbent polymer particles are mixed, if necessary, the lower layer absorbent body 23B and the upper layer absorbent body 23A can be wrapped with a wrapping sheet 24 such as a crepe paper (see FIG. 1, FIG. 7, and FIG. 9) integrally or separately.

The external form of the absorbent body 23 can be an appropriate shape such as a belt-like shape in which the front side part is relatively wider than the back side part, a rectangle shape, or a trapezoid shape, and a form in which a narrower part 23n with small width is formed at a predetermined middle part including the crotch portion C2 in the front-back direction is preferable. It is preferable that the minimum width W3 of the narrower part 23n is about 50 to 65% of the width W2 (the whole width of the absorbent body 23) of the non-narrower part located before and after the narrower part 23n. When the diaper front end is assumed to be 0% and the diaper back end is assumed to be 100%, it is preferable that the front end of the narrower part 23n is located within a range of 10 to 25%, it is preferable that the back end of the narrower part 23n is located within a range of 40 to 65%, and it is preferable that the site of the minimum width W3 of the narrower part 23n (the site of the minimum width) is located within a range of 25 to 30%.

When the absorbent body has the two-layer structure, it is preferable that the lower layer absorbent body is bigger, and thus, as in the embodiments shown in the drawings, it is preferable that the external form of the absorbent body is formed by the lower layer absorbent body, the shape thereof is formed into the narrow shape as described above, and the external form of the upper layer absorbent body is formed into a rectangle shape which is narrower than the width of the narrower part 23n.

The absorbent body 23 extends from the front side of the crotch portion C2 to the back side of the crotch portion C2 through the crotch portion C2, but it is enough that the absorbent body is provided from the crotch portion C2 to the back side of the crotch portion C2. In particular, when considering the application for men, the absorbent body is desirably provided from the front side to the back side of a scrotum-disposed region C1. The "scrotum-disposed region C1" refers to a region in the front-back direction in which the scrotum of a wearer is disposed, and the front side of the region C1 is a "front side region of the scrotum-disposed region C1" and the back side of the region C1 is a "back side region of the scrotum-disposed region C1." In the usual condition, the scrotum-disposed region C1 in the front-back direction has a length of about 80 to 100 mm.

(First embodiment of area for forming surface depression)

As shown in FIG. 1 to FIG. 4, characteristically, there is an elongated lower layer through section 60, which pierces in a thickness direction (i.e., there is no absorbent body) and extends in a front-back direction, at least on the center part of a width direction of a crotch portion C2 on a lower layer absorbent body 23B, and there is an upper layer through section 50, which pierces in a thickness direction (i.e., there is no absorbent body), at least within a range corresponding to the lower layer through section 60 in the front-back direction on an upper layer absorbent body 23A. The upper layer through section 50 has an elongated middle section 51, which is located above the lower layer through section 60 and extends in the front-back direction, and extending sections 52, which extend from both sides of a back side position of the middle section 51 in the width direction. Further, the side edge of the extending section 52 has a shape in which at least a part of the front side thereof is located further outside in the width direction toward the back side.

Figure 6:
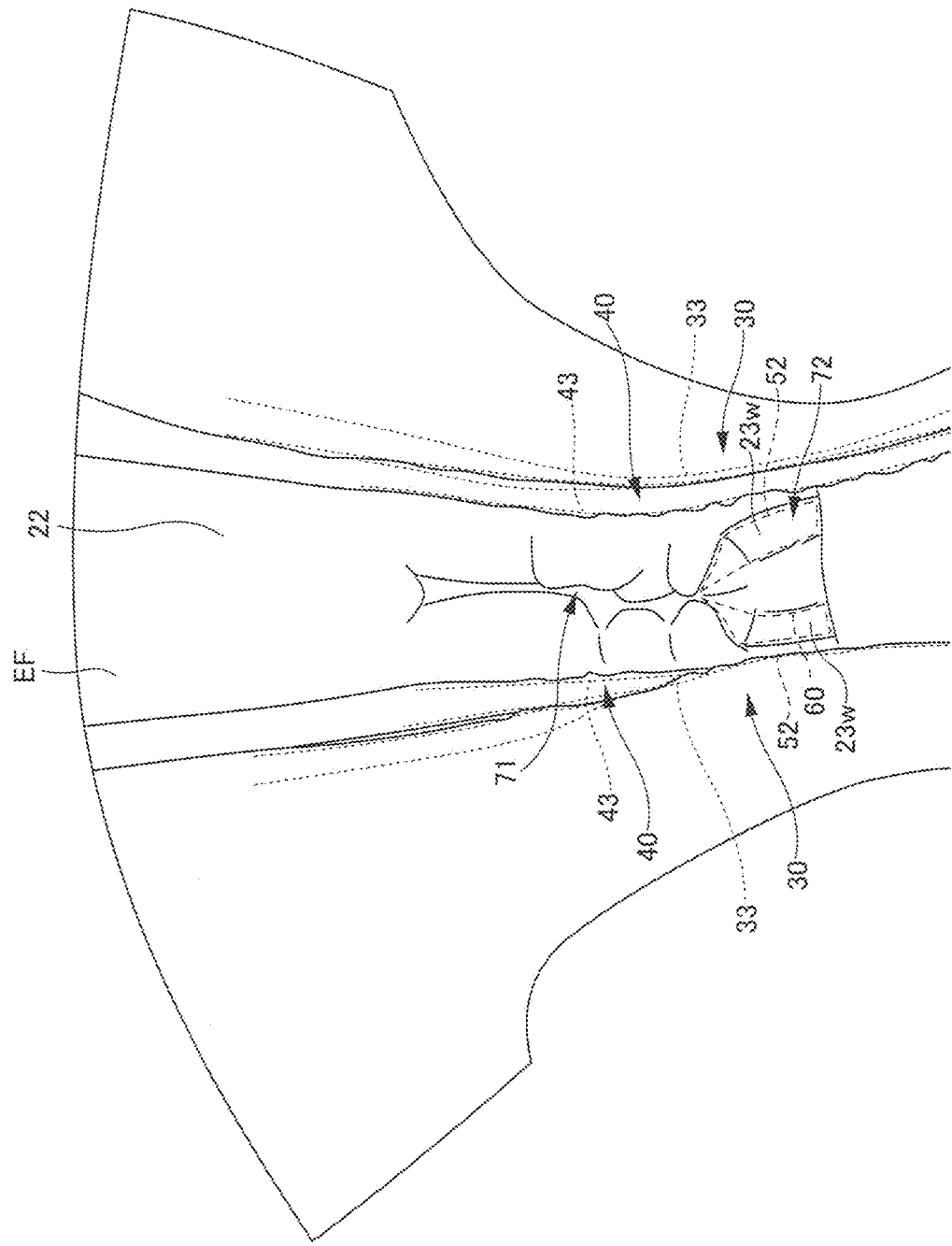
FIG. 6 is a perspective view of a wearing state.
Figure 8:
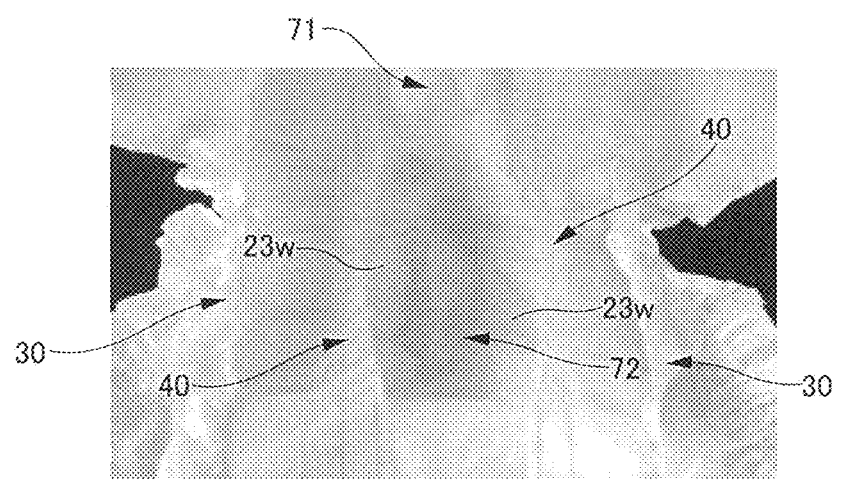
FIG. 8 is a photograph of a sample.

In the absorbent body 23 having such two-layer structure, there is no absorbent body 23 at an overlapped part (a first depression-formed part) of the lower layer through section 60 and the middle section 51 of the upper layer through section 50, the sites of the extending sections 52 (second depression-formed parts) of the upper layer through section 50 have a monolayer structure of the lower layer absorbent body 23B, and the outside parts of the extending sections 52 of the upper layer through section 50 have a two-layer structure of the upper layer absorbent body 23A and the lower layer absorbent body 23B. As shown in FIG. 6 to FIG. 9, when the disposable diaper is put between both legs and compressed in a width direction in a wearing state (see void arrows in FIG. 7 and FIG. 9), both side edges of the lower layer through section 60 and the upper layer through section 50 approach each other according to compression amount, because there is no absorbent body 23 at the overlapped part of the lower layer through section 60 and the middle section 51 of the upper layer through section 50. Thus, a narrow groove 71 is formed on a disposable diaper surface. At that time, though a force is also applied to monolayer structure parts 23w, which are located on the extending sections 52 of the upper layer through section 50, in a direction approaching each other, the monolayer structure parts 23w are easily folded to the underside along side edges of the extending sections 52 of the upper layer through section 50, which are boundaries with the two-layer structure part, because the side edge of the extending sections 52 of the upper layer through section 50 has a shape in which at least a part of the front side is located further outside in the width direction toward the back side (i.e., the right side edge is in a diagonally backward right direction, and the left side edge is in a diagonally backward left direction). Thus the monolayer structure parts 23w are folded to the underside toward the two-layer structure part of the outside thereof in the width direction and a part having no absorbent body between the monolayer structure parts 23w subsides toward the underside. Accordingly, as shown in FIG. 6 and FIG. 8, an almost boat-shaped depression 72 is formed on a disposable diaper surface. It would be difficult to form such deformation if the extending section 52 of the upper layer through section 50 had a rectangular shape (i.e., the side edge of the extending section 52 is U-shaped). Such boat-shaped depression can be easily restored to the compression in the width direction, not only that but the depth of the depression can be maintained because the monolayer structure part 23w, folded to the underside, serves as a wall, and thus the maintainability of the surface space is excellent. When urine is excreted, urine excreted in the front side of the depression area, which is not absorbed and moves on the diaper surface, flows backward in the large surface space as a passage, during which the urine is absorbed in the absorbent body 23 located on the back side. The conventional problem of diffusion block caused by the small surface space, accordingly, can be effectively prevented.

Figure 11C:
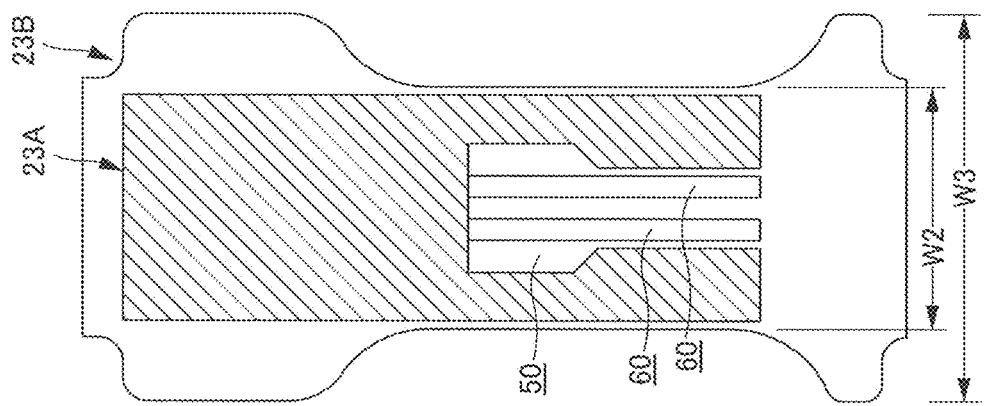
FIGS. 11(a) to (c) are plan views showing, respectively, (a) a lower layer absorbent body, (b) an upper layer absorbent body, and (c) a laminated state of the lower layer absorbent body and the upper layer absorbent body.
Figure 11B:
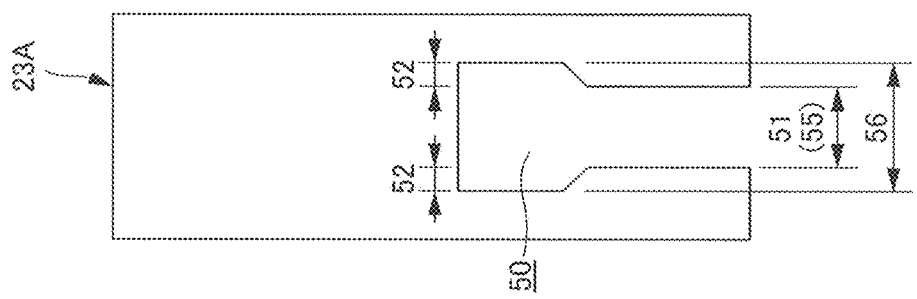
Figure 11A:
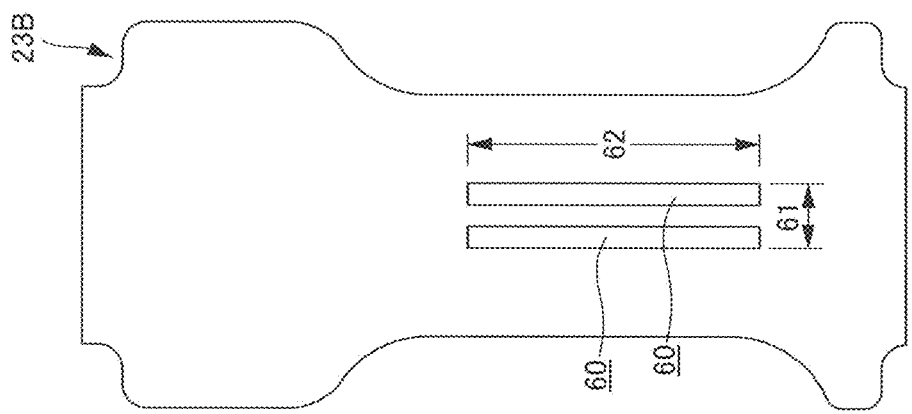
Figure 12A:
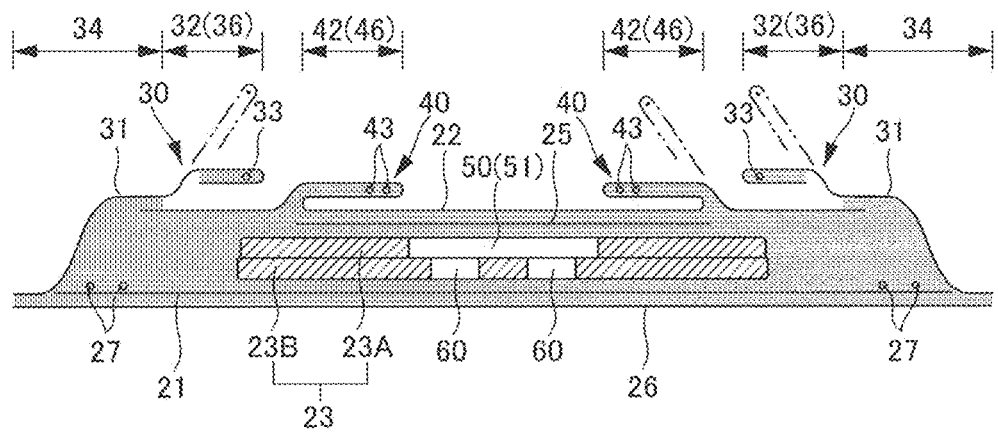
FIG. 12(a) is a cross-sectional view corresponding to a Z-Z cross-section in FIG. 1
Figure 12B:
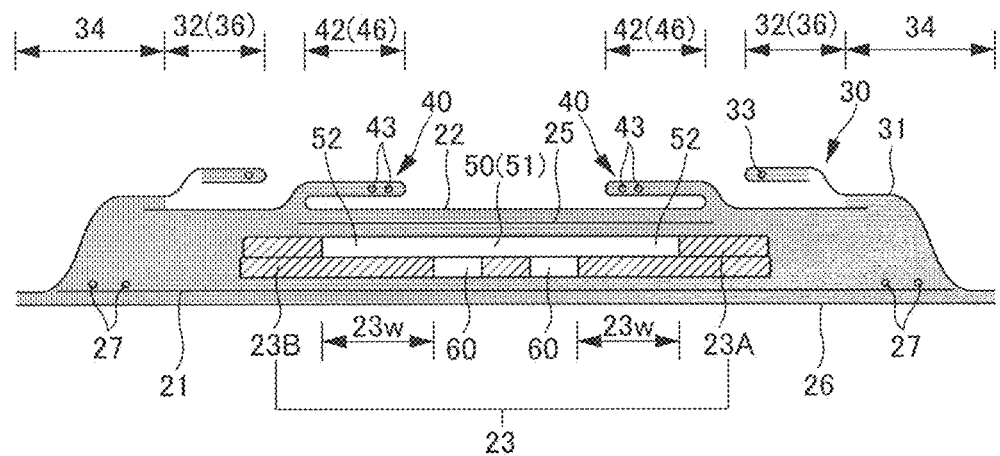
FIG. 12(b) is a view corresponding to an X-X cross-section in FIG. 1.
Figure 29A:
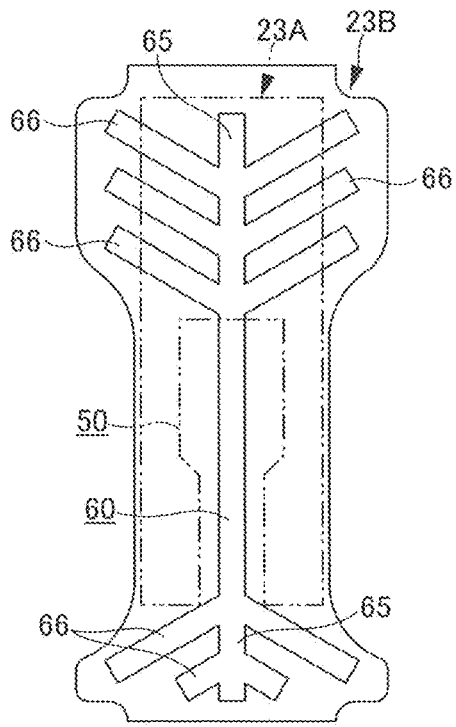
FIGS. 29(a) to (d) are plan views showing various variations of a lower layer absorbent body.
Figure 29B:
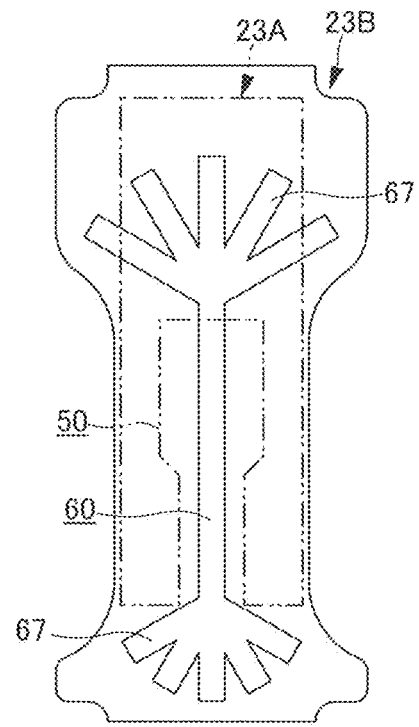
Figure 29C:
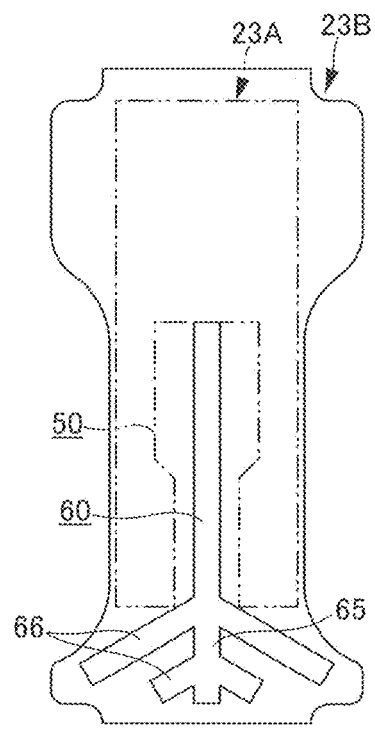
Figure 29D:
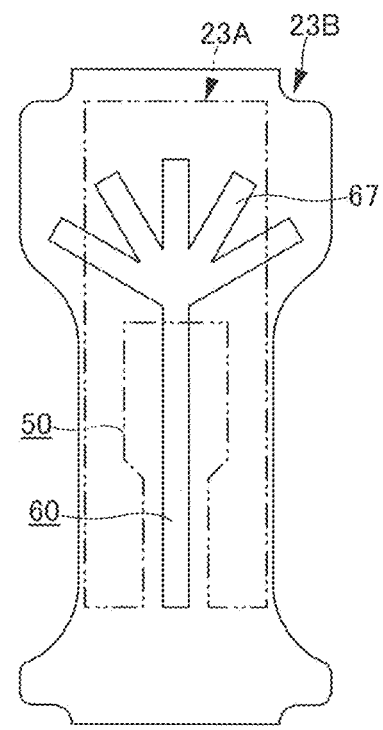

The shape of the lower layer through section 60 may be a rectangular shape of which width is constant in the front-back direction as in the embodiments shown in the drawings, and can be appropriately changed to, for example, a shape of which width is changed in the front-back direction (for example, the width is increased gradually toward the back side), so long as it is the elongated shape. A size of the lower layer through section 60 can be appropriately decided, and a length 62 in the front-back direction is preferably adjusted to about 180 to 210 mm, considering standard adults using this kind of disposable diaper. In addition, a width 61 of the lower layer through section 60 can be appropriately decided, and in usual, it is preferably adjusted to about 20 to 40 mm, because not so large width is preferable in order to secure shape-maintaining property of a space described later. As shown in FIG. 11 and FIG. 12, multiple lower layer through sections 60 may be provided at intervals in the width direction. In addition, as shown in FIG. 29(a), the front end of the lower layer through section 60 may be extended forward, for example, up to the front side part F2 and branched through sections 66 extending diagonally forward left and diagonally forward right from the extension part 65 may be provided, and the back end of the lower layer through section 60 may be extended backward, for example, up to the back side part B2 and branched through sections 66 extending diagonally backward left and diagonally backward right from the extension part 65 may be provided; as shown in FIG. 29(b), radially extension parts 67 radially extending forward, for example, up to the front side part F2 from the front end of the lower layer through section 60 may be provided, and radially extension parts 67 radially extending backward, for example, up to the back side part B2 from the back end of the lower layer through section 60 may be provided. In the examples shown in FIGS. 29(a) and 29(b), the extension parts 65 and the branched through sections 66 or the radially extension parts 67 are provided on both of the front side and the back side, but as shown in FIGS. 29(c) and 29(d), they may be provided either on the front side or the back side, or the shape thereof may be different between the front side and back side (for example, the extension part 65 and the branched through sections 66 are provided on either of the front side or the back side, and the radially extension parts 67 are provided on the other side, and the like).

It is desirable that the lower layer through section 60 is provided at a middle position of the lower layer absorbent body 23B in the front-back direction, i.e., the lower layer through section 60 is disposed so that it does not extend to reach the front and back ends of lower layer absorbent body 23B, whereby the stiffness of the absorbent body 23 is secured as a whole.

On the other hand, a size of the upper layer through section 50 can be appropriately decided, and a length thereof in the front-back direction may be the same as the length of the lower layer through section 60, as in the embodiments shown in the drawings, and may be shorter or longer than the length of the lower layer through section 60 (this also applies to the length of the middle section 51 in the front-back direction).

A width 55 of the middle section 51 of the upper layer through section 50 is desirably equal to or wider than the width 61 of the lower layer through section 60, and when considering the secure of the extending sections 52, it is desirable that the width 55 is about 1.2 to 1.5 times wider than the width 61 of the lower layer through section 60. A width 56 of the upper layer through section including the extending sections 52 (the total width of the width of the middle section 51 and the width of the extending sections 52) is desirably decided considering a size of the depression (mainly a height of the wall) or a shape-maintaining property of the depression, and the width 56 is desirably adjusted to about 1.5 to 2 times wider than the width 55 of the middle section 51, more specifically from about 36 to 120 mm.

Positions of the extending sections 52 of the upper layer through section 50 in the front-back direction can be appropriately decided. The extending section 52 may be formed by expanding sideward the upper layer through section 50 at the back side position thereof as in the embodiments shown in the drawings, or the extending section 52 may be formed by expanding sideward the upper layer through section 50 at the intermediate position thereof in the front-back direction. In addition to the embodiment shown in the drawing, the middle section 51 may be extended to the front side of the upper layer through section 50 and extending sections may be further provided at the both sides in the width direction of the middle section 51 at the front side position thereof so as to exhibit front-back symmetry between the extending sections 52 of the back side position and those of the front side position. In this case, a pair of boat-shaped depressions face to each other through a narrow groove 71 in a longitudinal direction (an almost sandglass-shaped depression is formed) in a wearing state.

Figure 10A:
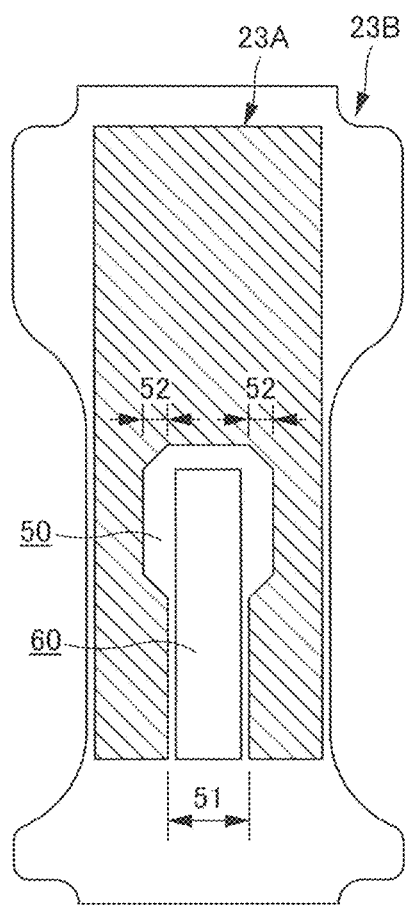
FIGS. 10(a) and (b) are plan views showing main parts of various shapes of an upper layer through section.
Figure 10B:
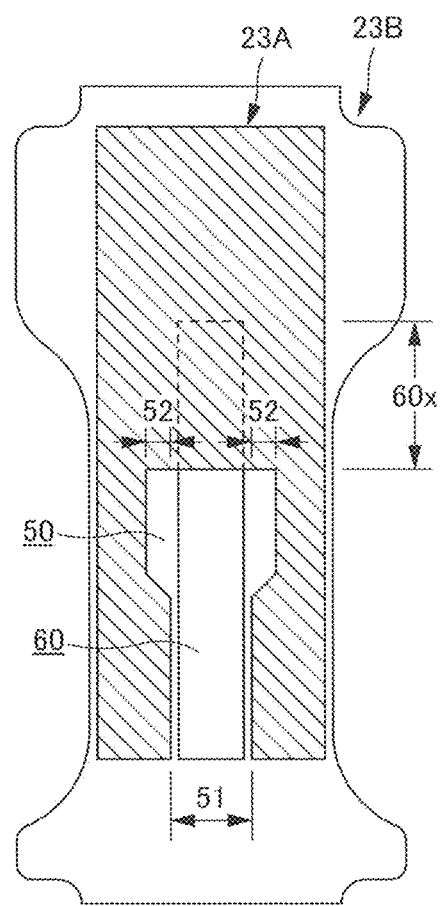
Figure 13C:
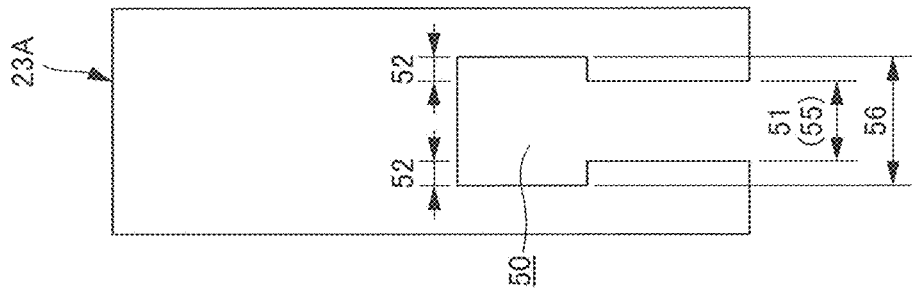
FIGS. 13(a) to (c) are plan views showing various upper layer absorbent bodies.
Figure 13B:
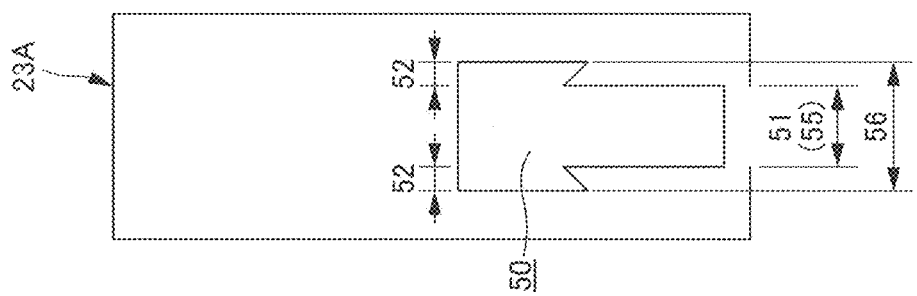
Figure 13A:
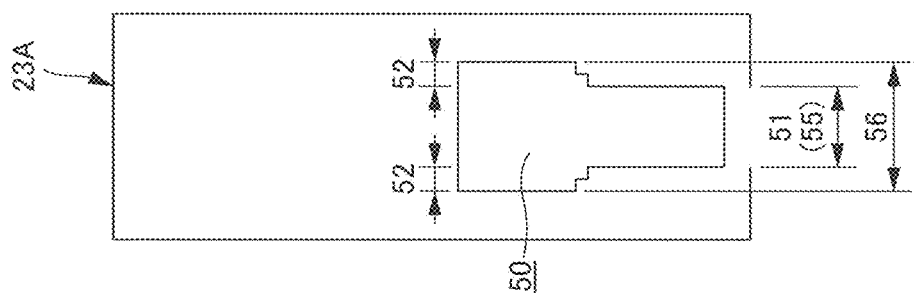

A shape of the middle section 51 excluding the extending sections 52 in the upper layer through section 50 may be the rectangular shape of which width is constant in the front-back direction as in the embodiments shown in the drawings, and can be appropriately changed, for example, to a shape of which width is changed in the front-back direction (for example, the width is gradually widened toward the back side), and the like. With respect to a shape of the extending section 52 of the upper layer through section 50, a shape of the side edge thereof may be a bending line as in the embodiments shown in the drawings, or may be a curve line such as a circular arc. In the embodiments shown in the drawings, the shape is a trapezoid in which a boundary with the middle section 51 is a base line and the back edges are at right angles to the base line (a shape including the extending sections 52 and the middle section 51 is a pentagon) so that at least a part of the front side of the side edge of the extending section 52 is located further outside in the width direction toward the back side. The shape may be a trapezoid as shown in FIG. 10(*a*) (a shape including the extending sections 52 and the middle section 51 between them is a hexagon). A shape of the side edge of the extending section 52 may be, for example, a shape in which a part of the front side is located stepwise further outside in the width direction toward the back side as shown in FIG. 13(*a*), a shape in which a part of the front side is located gradually further outside in the width direction toward the front side as shown in FIG. 13(*b*), or a rectangular shape as shown in FIG. 13(*c*).

A position of the upper layer through section 50 in the front-back direction may be appropriately decided. The front end (front end of the middle section 51) is preferably located at the same position as or in the front side position of the front end of the lower layer through section 60, but it may be located in the back side position thereof. The back end of the upper layer through section 50 is preferably located at the same position as or the back side position of the back end of the lower layer through section 60 as in the embodiments shown in the drawings, but it is also preferable that it is located in front of the position thereof. Examples of the latter case may include, as shown in FIG. 10(*b*), a form in which the lower layer through section 60 is extended backward from the back end of the upper layer through section 50 and backward from the crotch portion C2 (the reference sign 60*x* designates this extending part). In that case, when urine passes through the lower layer through section 60 and enters the under part of the upper layer absorbent body 23A, the return to the skin is blocked by the upper layer absorbent body 23A.

The middle section 51 of the upper layer through section 50 extends to the front end of the upper layer absorbent body 23A and opens to the front end of the upper layer absorbent body 23A, and the front end of the upper layer absorbent body 23A is located at the same position as or the back side position of the front end of the lower layer through section 60 in the embodiments shown in the drawings. By doing so, when the crotch portion C2 is compressed in the width direction, higher compression is likely to be applied toward the front side of the upper layer absorbent body 23A and the front side of the upper layer through section 50. Thus, the boat-shaped depression can be easily formed.

Figure 14C:
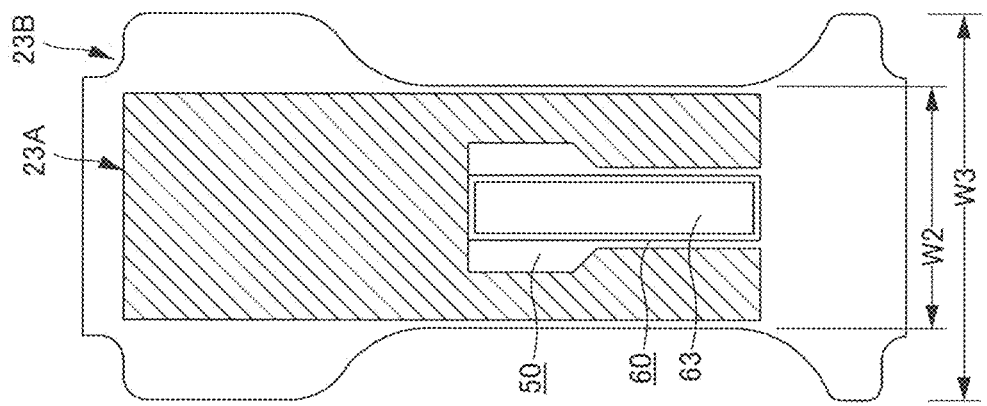
FIGS. 14(a) to (c) are plan views showing, respectively, (a) a lower layer absorbent body, (b) an upper layer absorbent body, and (c) a laminated state of the lower layer absorbent body and the upper layer absorbent body.
Figure 14B:
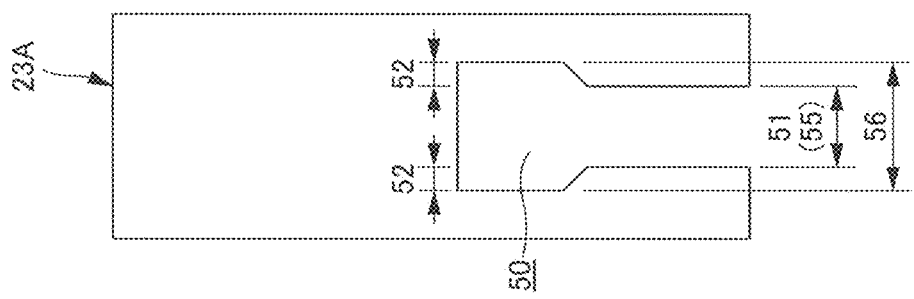
Figure 14A:
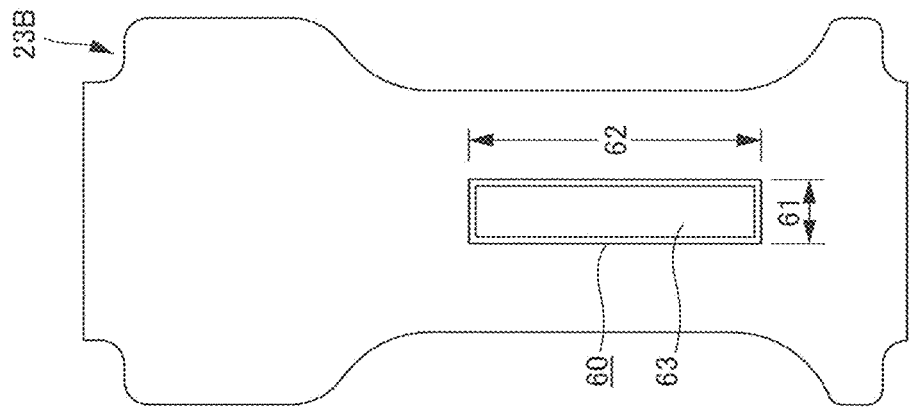
Figure 15A:
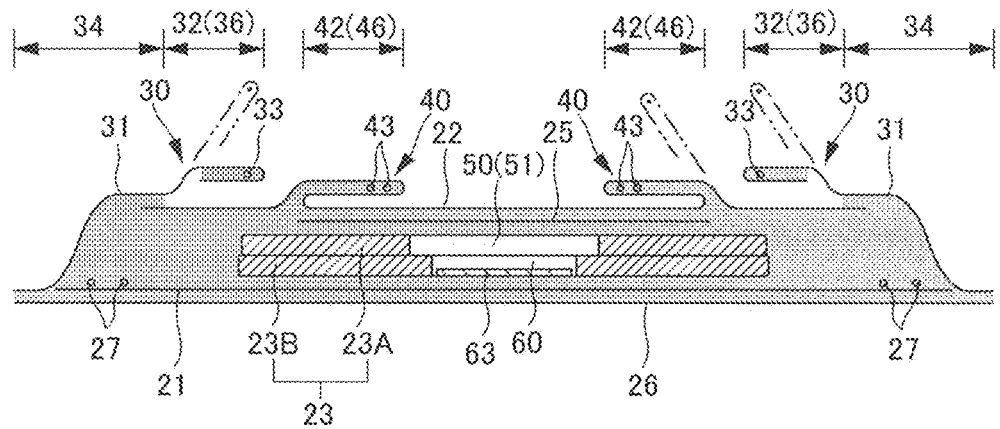
FIG. 15(a) is a cross-sectional view corresponding to a Z-Z cross-section in FIG. 1
Figure 15B:
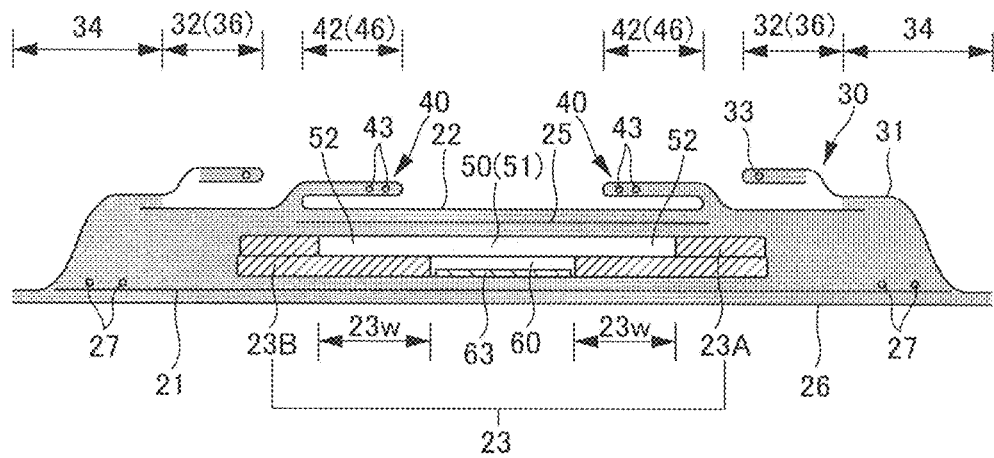
FIG. 15(b) is a view corresponding to an X-X cross-section in FIG. 1.
Figure 16:
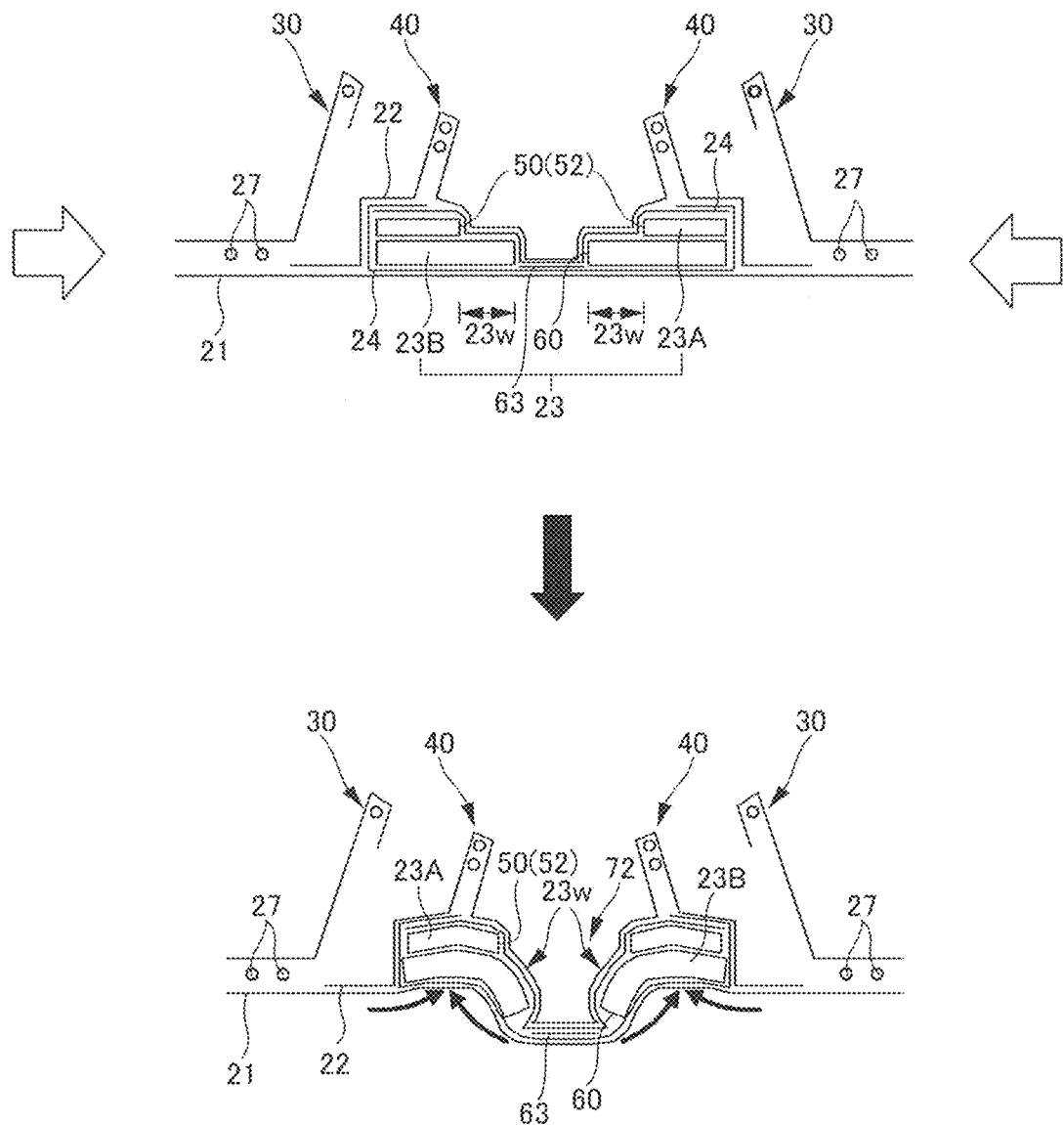
FIG. 16 is a schematic cross-sectional view showing change of a state before and after wearing.

In the embodiments shown in the drawings, high diffusibility of urine can be secured, because there is no absorbent body in the site of the overlapped part with the lower layer through section, however, the passage formed of the lower layer through section is easily deformed and is likely to be broken down. As shown in FIG. 14 to FIG. 16, accordingly, when a diffusion sheet 63 capable of promoting the diffusion of urine in the front-back direction is provided on the bottom of the lower layer through section, the passage of the lower layer through section is easily maintained, and the diffusion of urine passing through the lower layer through section in the front-back direction is promoted.

A kind of the material of the diffusion sheet 63 is not particularly limited so long as it can promote the diffusion of urine in the front-back direction, and non-woven fabrics and plastic sheets can be used, and a filament assembly of tows of synthetic fiber (fiber bundles) such as cellulose acetate, which are may be subjected to opening if necessary, can also be used.

As the fiber material forming the non-woven fabric, regenerated fibers such as rayon and cupra and natural fibers such as cotton may be used, in addition to synthetic fibers including olefin fibers such as polyethylene and polypropylene, polyester fibers, and amide fibers. The non-woven fabric has preferably a basis weight of about 10 to 40 g/m². When the plastic sheet is used, sheet having a hollow structure obtained by bonding multiple plastic sheets can be used, in addition to sheets on which groove structures are provided on the surface thereof in the front-back direction. Non-woven fabric-based sheets with which high absorbent polymer particles are mixed or to which the polymer particles are adhered if necessary may also be used.

When the filament assembly is used, a fiber basis weight thereof can be adjusted to about 30 to 120 g/m². Fineness thereof is from 1 to 16 dtex, preferably from 1 to 10 dtex, more preferably from 1 to 5 dtex. The filament may be a non-crimped fiber, but is preferably a crimped fiber. The crimped fiber has a degree of crimp of, for example, about 5 to 75 crimps, preferably about 10 to 50 crimps, more preferably about 15 to 50 crimps per inch. A uniformly crimped fiber is often used.

Although it is preferable that the diffusion sheet 63 is provided throughout the lower layer through section 60, the sheet may be provided on a part thereof in the front-back direction or in the width direction. The diffusion sheet 63 may be provided between the top sheet 22 and the liquid-impermeable sheet 21 as in the embodiments shown in the drawings, or may be bonded to the surface of the top sheet 22, so long as it is provided on the bottom of the lower layer through section When the diffusion sheet 63 is provided, it is preferable that the top sheet is directly or indirectly melted to the diffusion sheet 63 by subjecting to heating-pressurizing such as heat embossing from the top sheet 22, because the stiffness of the bottom of the lower layer through section is increased, and it is difficult to break the passage of the lower layer through section.

(Three-Dimensional Gather at Crotch Portion)

In the embodiments shown in the drawings, three-dimensional gathers 40 at the crotch portion extend at both sides of the diaper surface in the width direction, the three-dimensional gather has a projecting portion 42, which projects from a lateral side of the upper layer through section 50 and which extends in the front-back direction, the projecting portion contains non-standing parts 45, which are fixed in a fallen state and which are positioned in a front side and in a back side of the projecting portion 42 respectively, and a standing part 46, which is not fixed, which is disposed between the non-standing parts 45, and which has a resilient and elastic gather member 43 fixed in a stretched state in the front-back direction. The standing part 46 has resilient and elastic gather members fixed in a stretched state in the front-back direction. The standing part 46 is a part which stands from the diaper surface, as shown by two-dot chain lines in FIG. 4, by applying a contracting force owing to the resilient and elastic gather member 43.

The three-dimensional gather 40 at the crotch portion may not be provided, however, it is preferable to provide it separately from the three-dimensional gather 30 at the side part, because the absorption amount at the crotch portion C2 must be decreased due to the presence of the upper layer through section 50 and the lower layer through section 60, thereby the urine would easily move there.

In order to form the three-dimensional gather 40 at the crotch portion, it is preferable that side parts from the upper layer through section 50 in the top sheet 22 are folded up to form the projecting portions 42 as in the embodiments shown in the drawings, although it is possible to form the three-dimensional gather 40 at the crotch portion by attaching another sheet on the diaper surface.

When the three-dimensional gather 40 at the crotch portion is provided, it is preferable that the extending section 52 of the upper layer through section 50 is located between the non-standing parts 45 of the three-dimensional gather 40 at the crotch portion in the front-back direction (i.e., the position of the extending section 52 of the upper layer through section 50 in the width direction is overlapped with the position of the non-standing part 45 of the three-dimensional gather 40 at the crotch portion in the width direction), because the contracting force owing to the resilient and elastic gather member 43 of the three-dimensional gather 40 at the crotch portion can be effectively acted on the monolayer structure part 23*w*, the formation of the boat-shaped depression is promoted, and the shape-maintaining property of the depression is improved. However, the non-standing part 45 of the three-dimensional gather 40 at the crotch portion may also be located at the center side or the outside of the extending sections 52 of the upper layer through section 50 in the width direction.

The position of the base end of the projecting portion 42 in the width direction in the three-dimensional gather 40 at the crotch portion is desirably separated sideward from the extending sections 52 as shown in the embodiments shown in the drawings, but it can be aligned with the side edge of the extending section 52, or can be located within the extending section 52. In particular, it is most preferable that a position of a base end of the extending section 42 in the width direction in the three-dimensional gather 40 at the crotch portion is located on the outside of the extending sections 52 of the upper layer through section 50 and on the two-layer structure parts of the upper layer absorbent body 23A and the lower layer absorbent body 23B in the developed state. It is most preferable that a position of a front edge of the extending section 42 in the width direction in the three-dimensional gather 40 at the crotch portion is located on a part passing through the monolayer structure part 23*w* in the developed state. Due to the above locations, the monolayer structure part 23*w* can be easily folded to the underside along the side edge of the extending sections 52 of the upper layer through section 50, which is the boundary with the two-layer structure part, so that the boat-shaped depression 72 can be formed and maintained reliably.

A material and a stretch rate during fixing of the resilient and elastic gather member 43 in the three-dimensional gather 40 at the crotch portion may be appropriately selected from the same materials and the same ranges as used in the three-dimensional gather 30 at the side part. In case where the three-dimensional gather 40 at the crotch portion is formed separately from the top sheet by attaching a dedicated sheet on the diaper surface, and also in case where a part of top sheet, which is located at the lateral side of the upper layer through section 50, is folded up to form the three-dimensional gather 40 at the crotch portion as in the embodiments shown in the drawings, it is preferable to use a water-repellent top sheet in at least an area of the three-dimensional gather 40 at the crotch portion, in particular, at least the area for forming surface depression, because the diffusion to the dorsal side can be promoted by using the water-repellant top sheet.

A size of each part of the three-dimensional gather 40 at the crotch portion can be appropriately decided, and a space between the non-standing parts 45 in the front-back direction is preferably adjusted to about 150 to 180 mm, and a space between the base ends of the projecting portion 42 in the width direction is preferably adjusted to about 60 to 80 mm, considering standard adults using this kind of disposable diaper. It is also preferable that the standing part 36 of the three-dimensional gather 30 at the side part is formed so that it extends forward and backward from the standing part 46 of the three-dimensional gather 40 at the crotch portion in the front-back direction.

In the embodiments shown in the drawings, the three-dimensional gather 40 at the crotch portion extends over the full length L of the disposable diaper (provided that the length of the non-standing part 45 in the front-back direction is longer than the length of the three-dimensional gather 30 at the side part), but it may be a length from the vicinity of the front side to the vicinity of the back side of the length of the extending sections 52 of the upper layer through section 50 in the front-back direction, considering a common producing method in which the disposable diaper is assembled while the materials are conveyed in the front-back direction of the disposable diaper.

(Second Embodiment of Area for Forming Surface Depression)

Figure 17C:
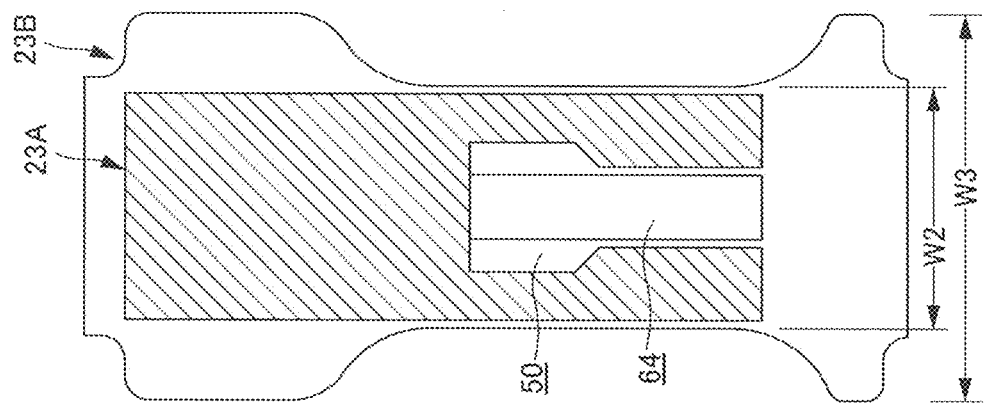
FIGS. 17(a) to (c) are plan views showing, respectively, (a) a lower layer absorbent body, (b) an upper layer absorbent body, and (c) a laminated state of the lower layer absorbent body and the upper layer absorbent body.
Figure 17B:
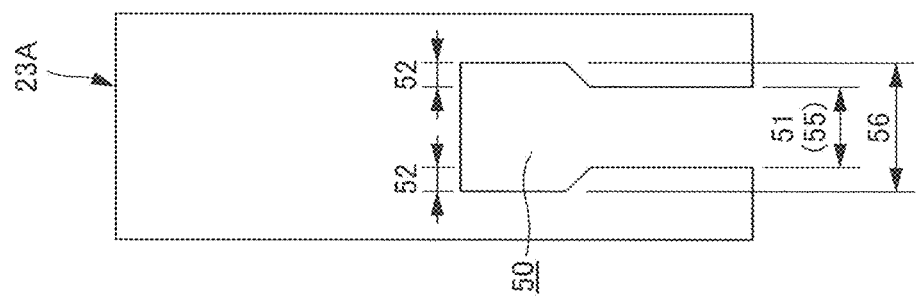
Figure 17A:
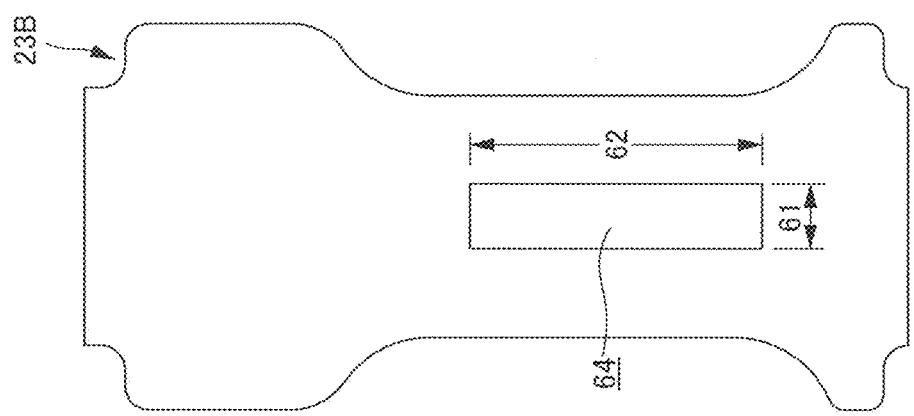
Figure 18A:
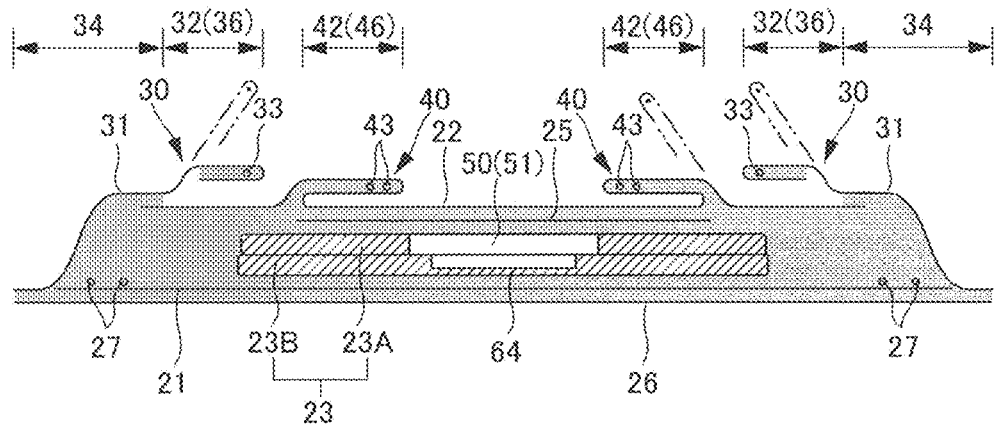
FIG. 18(a) is a cross-sectional view corresponding to a Z-Z cross-section in FIG. 1
Figure 18B:
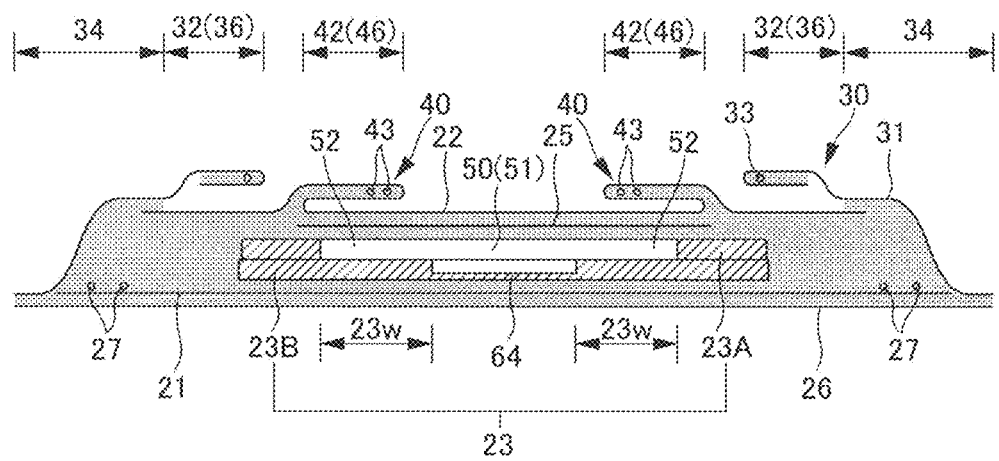
FIG. 18(b) is a view corresponding to an X-X cross-section in FIG. 1.
Figure 19:
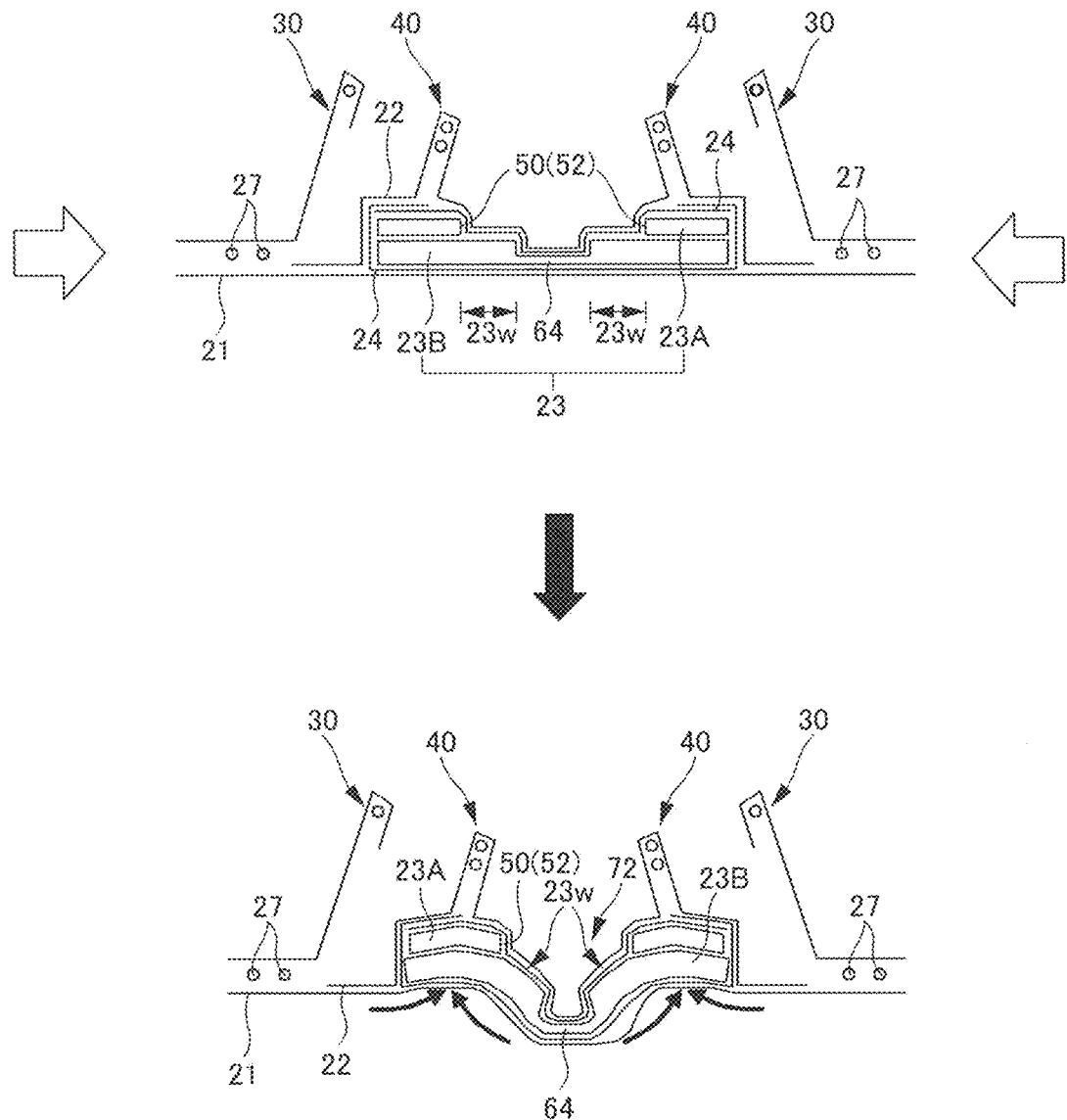
FIG. 19 is a schematic cross-sectional view showing change of a state before and after wearing.
Figure 20C:
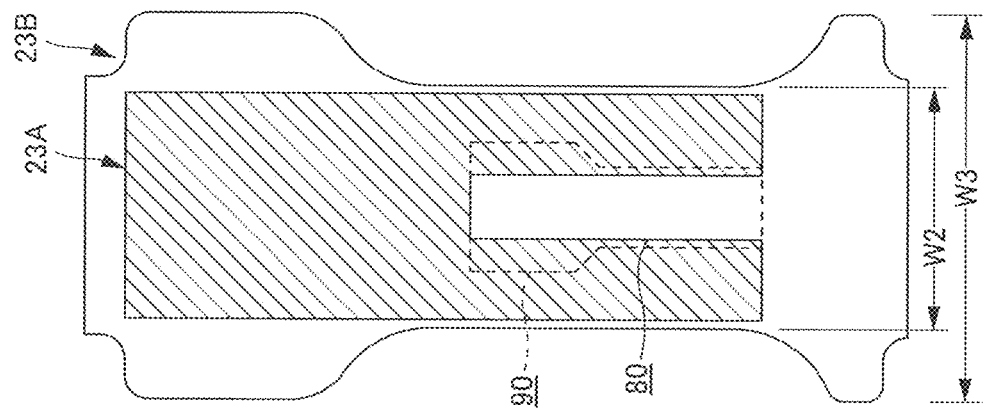
FIGS. 20(a) to (c) are plan views showing, respectively, (a) a lower layer absorbent body, (b) an upper layer absorbent body, and (c) a laminated state of the lower layer absorbent body and the upper layer absorbent body.
Figure 20B:
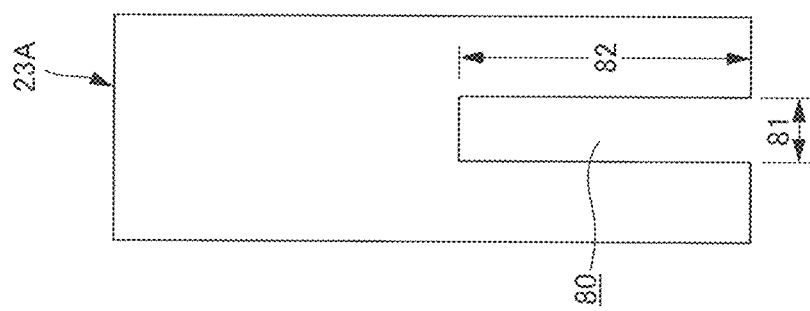
Figure 20A:
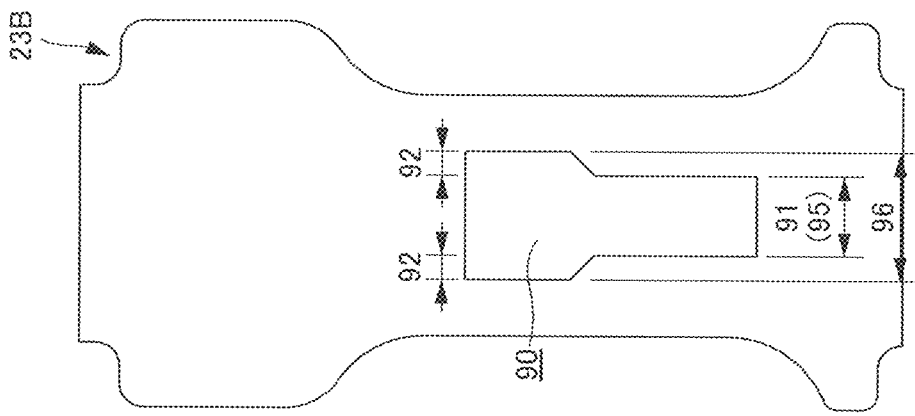

Even if a lower layer thin section 64, which is thinner than the periphery thereof (which is not pierced in the thickness direction), as shown in FIG. 17 to FIG. 19, is formed instead of the lower layer through section 60 of the lower layer absorbent body 23B in the first embodiment, almost the same advantages as obtained in the first embodiment can be obtained. According to the second embodiment, an overlapped part (a first depression-formed part) of the lower layer thin section 64 and the middle section 51 of the upper layer through section 50 has a monolayer structure of the lower layer thin section 64, the site of the extending section 52 (a second depression-formed part) of the upper layer through section 50 has a monolayer structure of a part 23*w* excluding the thin section of the lower layer absorbent body 23B, and the outside part of the extending section 52 of the upper layer through section 50 has a two-layer structure of the upper layer absorbent body 23A and the lower layer absorbent body 23B. When the disposable diaper is put between both legs and compressed in the width direction in a wearing state, though forces are applied to the monolayer structure parts 23*w* located on the extending sections 52 of the upper layer through section 50 in a direction approaching each other, the monolayer structure parts 23*w* are folded to the underside toward the two-layer structure parts of the outside thereof in the width direction, because the monolayer structure parts 23*w* are easily folded to the underside along side edges of the extending sections 52 of the upper layer through section 50, which are boundaries with the two-layer structure parts, and a part between the both monolayer structure parts 23*w* subsides toward the underside, whereby a wide depression is formed on the disposable diaper surface. Such depression can be easily restored to the compression in the width direction, not only that but the depth of the depression can be maintained because the monolayer structure part 23*w*, folded to the underside, serves as a wall, and thus the maintainability of the depression and further the maintainability of the surface space are excellent. Also in the second embodiment, when urine is excreted, urine excreted in the front side of the depression area, which is not absorbed and moves on the diaper surface, flows backward in the large surface space as a passage, during which the urine is absorbed in the absorbent body 23 located on the back side. The conventional problem of diffusion block caused by the small surface space, accordingly, can be effectively prevented.

A thickness of the lower layer thin section 64 is not particularly limited, and it can be adjusted to about 10 to 50% of the thickness of parts excluding the thin section, and usually adjusted to about 1 to 5 mm. The lower layer thin section is not limited by a specific forming method, and for example, it can be formed by decreasing a basis weight thereof so as to be lower than that of the periphery thereof, or by compressing in the thickness direction (if necessary, heating can be added).

The others including the alternative versions are the same as in the first embodiment, and the same explanations in the first embodiment can also be applied to the second embodiment except that the lower layer through section 60 is changed to the lower layer thin section 64, and thus further explanations are intentionally omitted.

(Third Embodiment of Area for Forming Surface Depression)

Figure 21A:
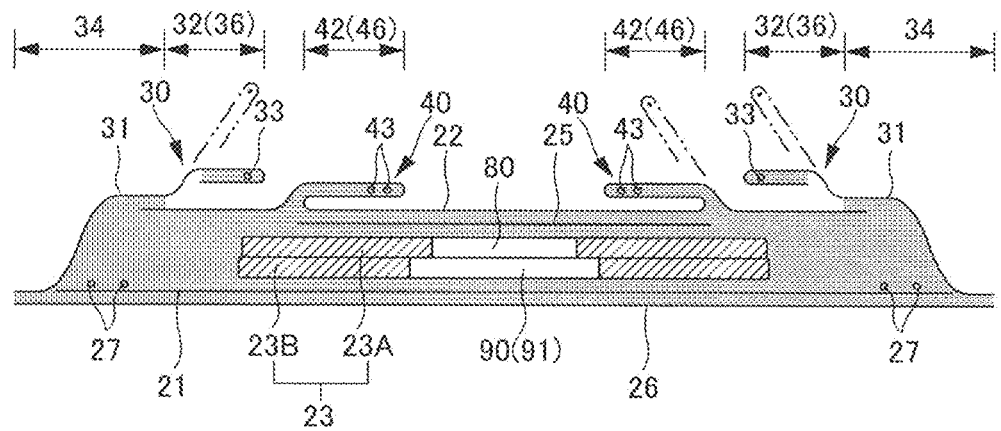
FIG. 21(a) is a cross-sectional view corresponding to a Z-Z cross-section in FIG. 1
Figure 21B:
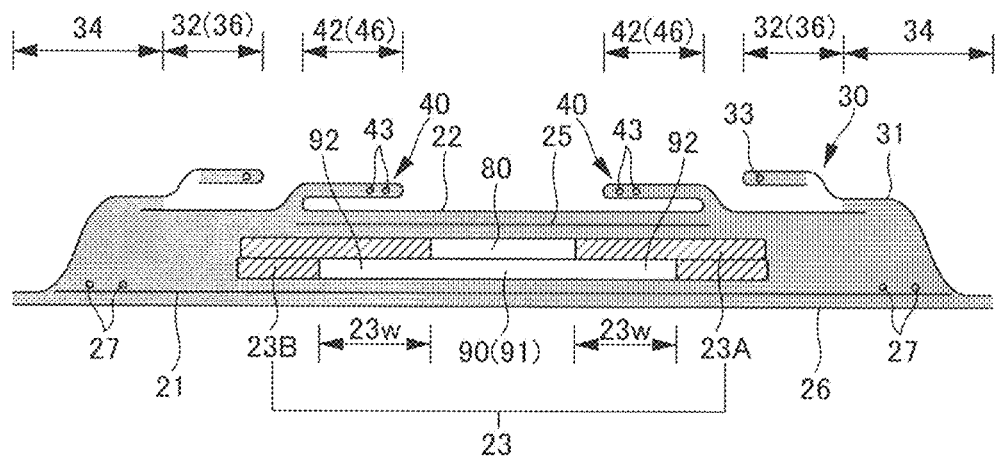
FIG. 21(b) is a view corresponding to an X-X cross-section in FIG. 1.
Figure 22:
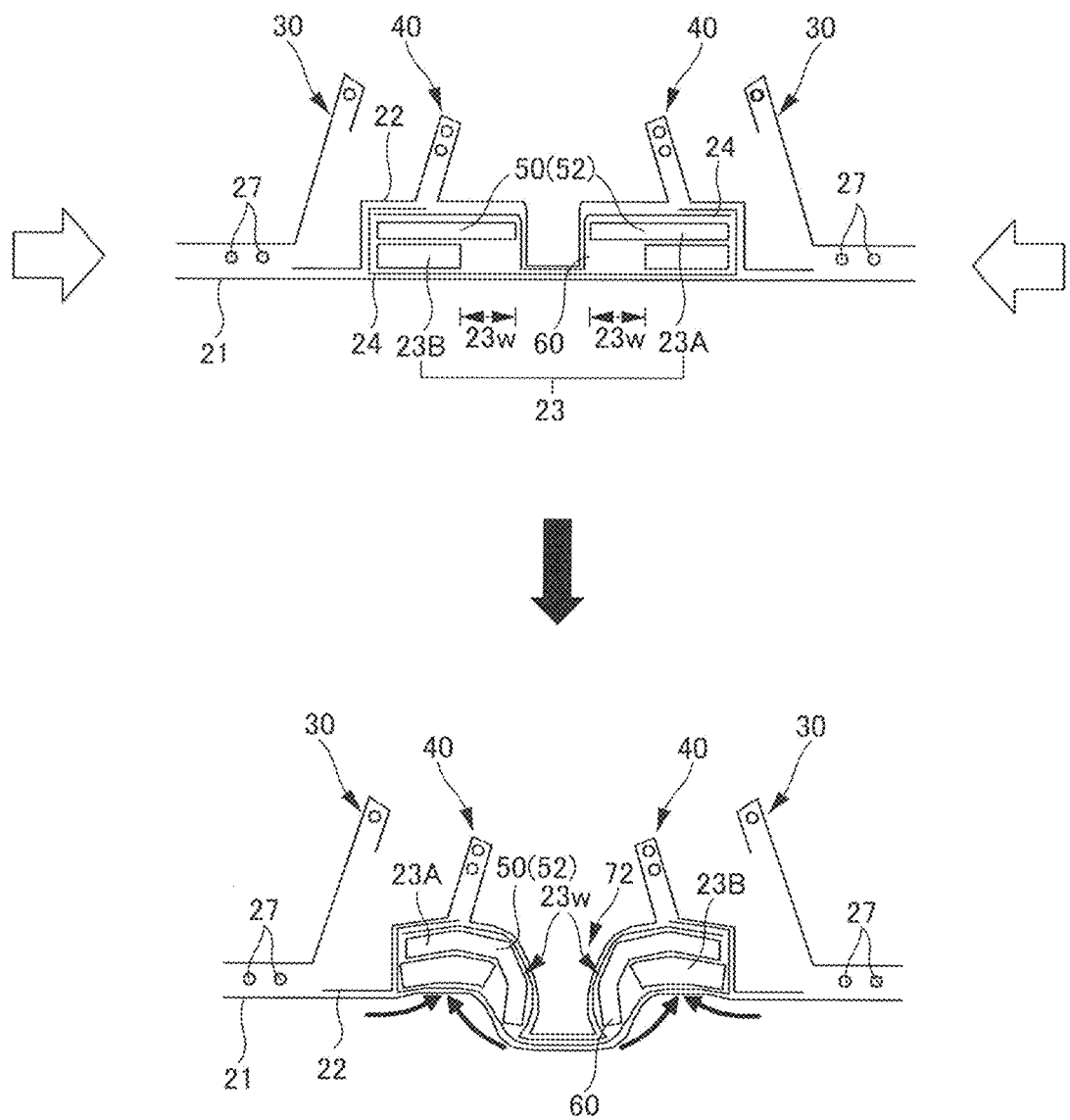
FIG. 22 is a schematic cross-sectional view showing change of a state before and after wearing.
Figure 23:
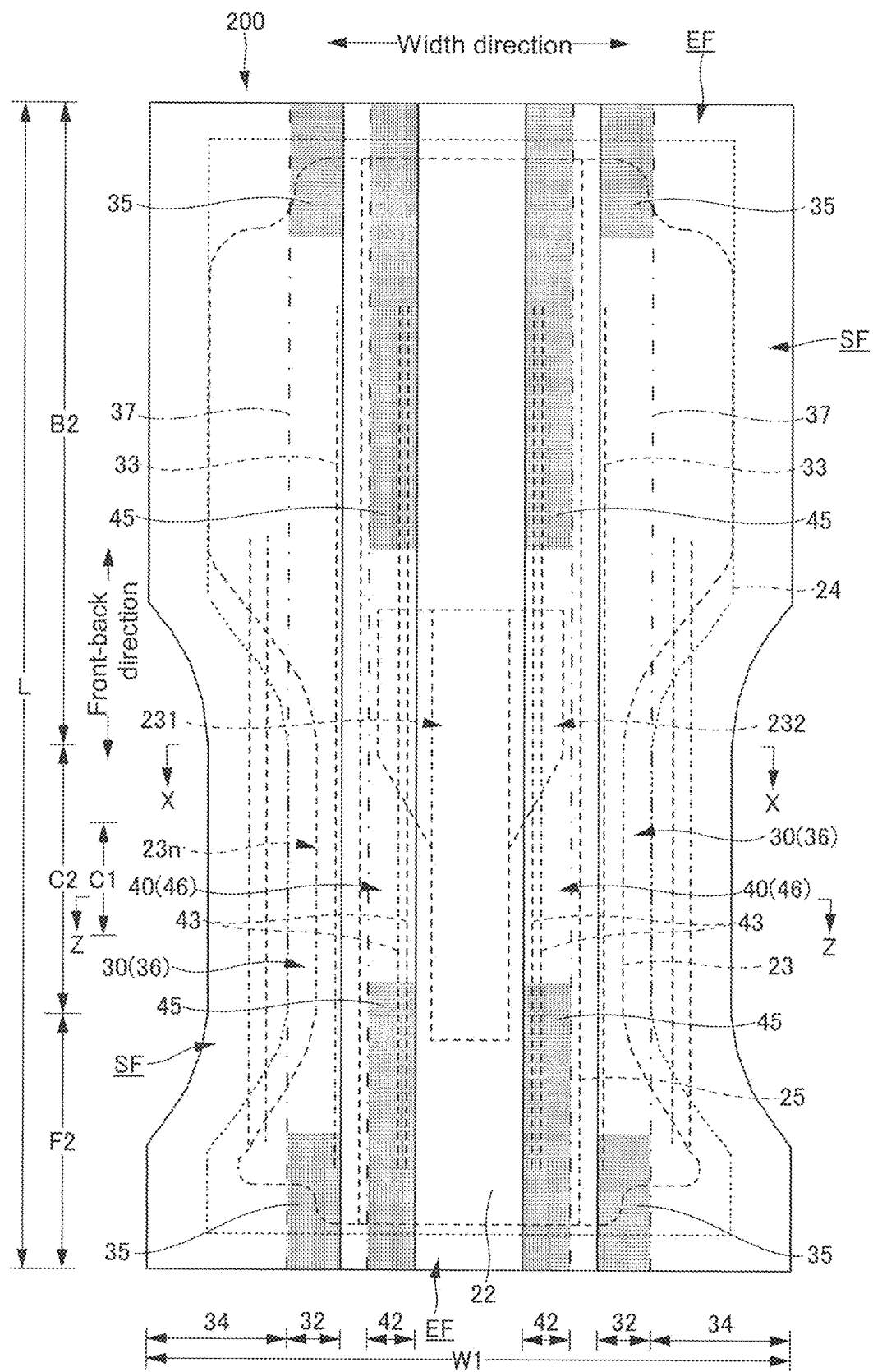
FIG. 23 is a plan view showing an inner-surface side of a pad-type disposable diaper in a developed state.
Figure 24:
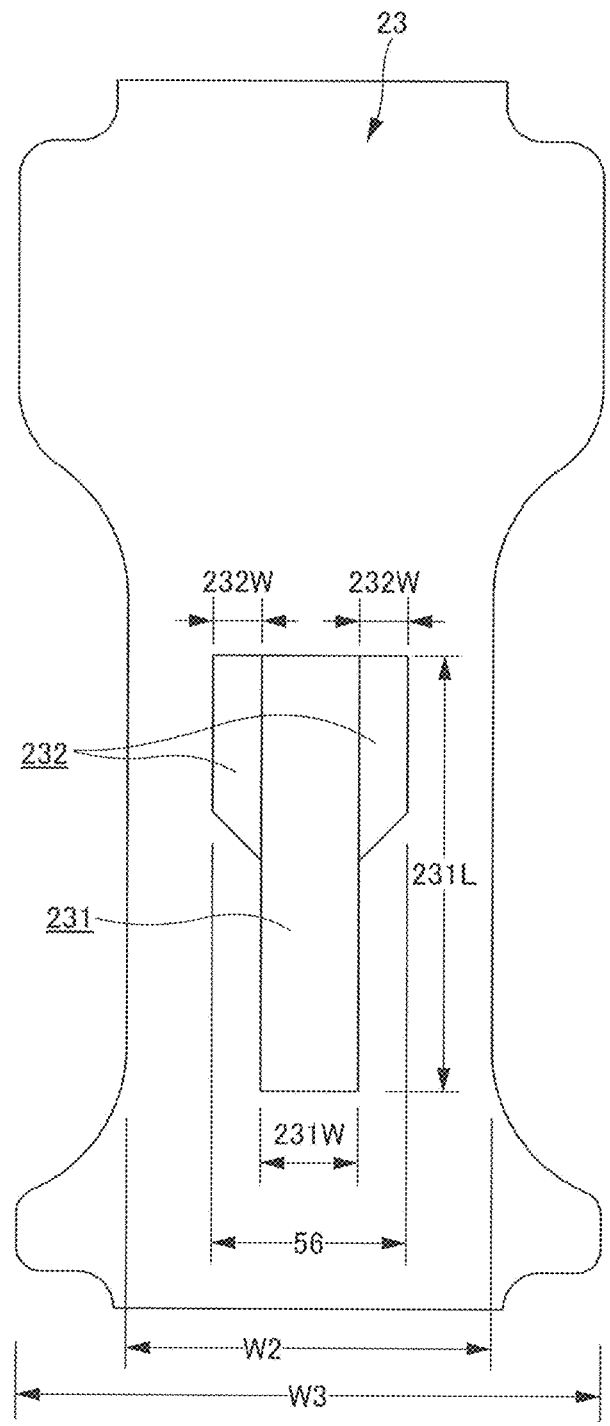
FIG. 24 is a plan view showing an absorbent body.
Figure 25A:
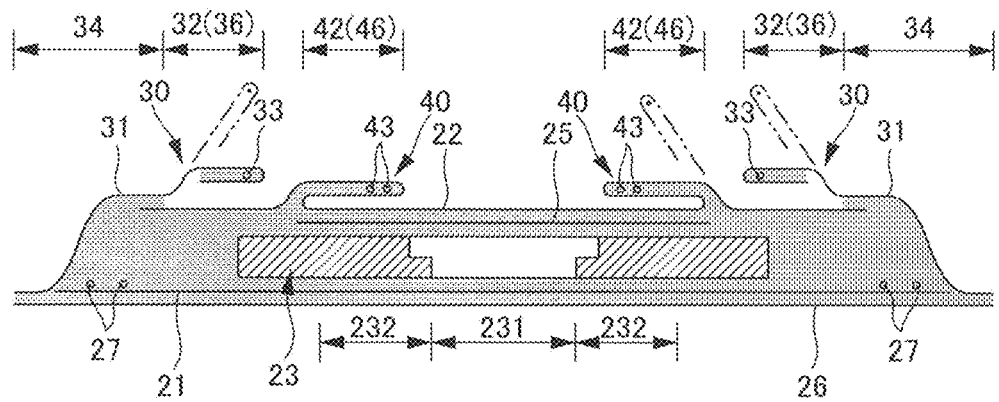
FIG. 25(a) is a Z-Z cross-sectional view in FIG. 23
Figure 25B:
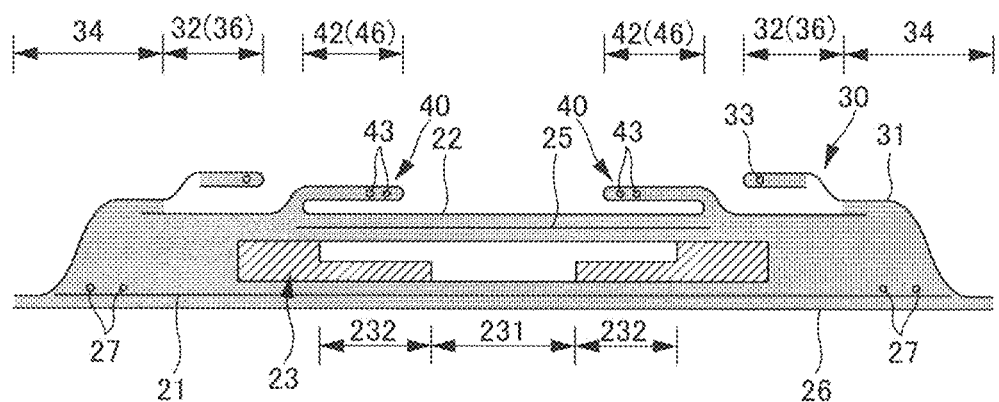
FIG. 25(b) is an X-X cross-sectional view in FIG. 23.
Figure 26:
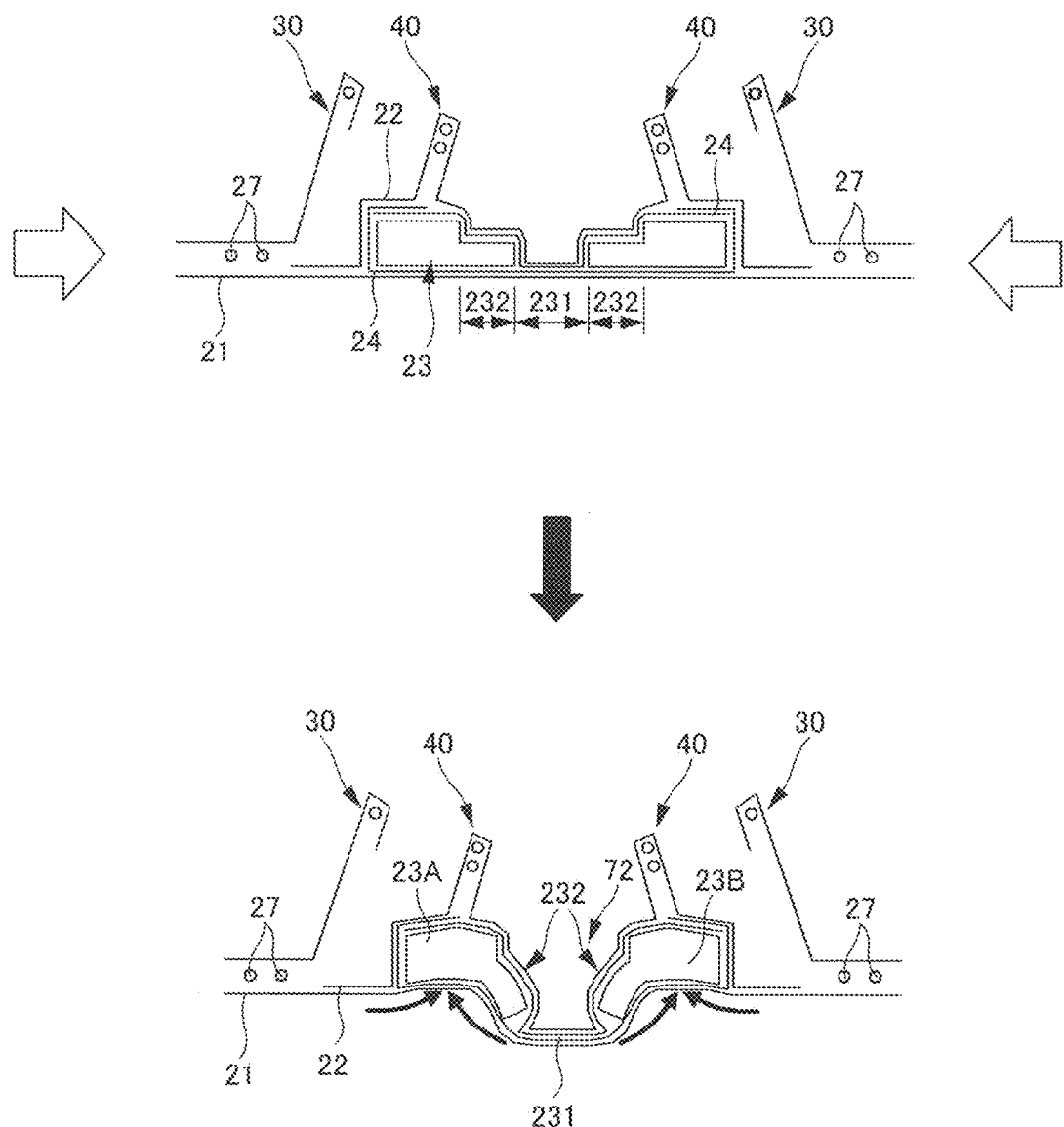
FIG. 26 is a schematic cross-sectional view showing change of a state before and after wearing.

Even if the shapes of the upper layer through section and the lower layer through section in the first embodiment are upside down, as shown in FIG. 21 and FIG. 22, the same advantages can be obtained. Reference sign 80 in FIG. 21 and FIG. 22 designates an upper layer through section, reference sign 81 designates a width of the upper layer through section 80, reference sign 82 designates a length of the upper layer through section 80 in the front-back direction, reference sign 90 designates a lower layer through section, reference sign 91 designates a middle section of the lower layer through section 90, reference sign 92 designates an extending section of the lower layer through section 90, reference sign 95 designates a width of the middle section 91, reference sign 96 designates a width of the lower layer through section 90 including the extending sections 92. According to the third embodiment, the overlapped part (a first depression-formed part) of the upper layer through section 80 and the middle section 91 of the lower layer through section 90 has a structure having no absorbent body 23, the site of the extending section 92 (a second depression-formed part) of the lower layer through section 90 has a monolayer structure of the upper layer absorbent body 23A, and the outside part of the extending section 92 of the lower layer through section 90 has a two-layer structure of the lower layer absorbent body 23B and the upper layer absorbent body 23A. When the disposable diaper is put between both legs and compressed in the width direction in a wearing state, though forces are applied to the monolayer structure parts 23w located on the extending sections 92 of the lower layer through section 90 in a direction approaching each other, the monolayer structure parts 23w are folded to the underside toward the two-layer structure part of the outside thereof in the width direction, because the monolayer structure parts 23w are easily folded to the underside along side edges of the extending sections 92 of the lower layer through section 90, which are boundaries with the two-layer structure part, and a part between the monolayer structure parts 23w subsides toward the underside, whereby a wide depression is formed on the disposable diaper surface. Such depression can be easily restored to the compression in the width direction, not only that but the depth of the depression can be maintained because the monolayer structure part 23w, folded to the underside, serves as a wall, and thus the maintainability of the depression and further the maintainability of the surface space are excellent. Also in the invention according to this claim, when urine is excreted, urine excreted in the front side of the depression area, which is not absorbed and moves on the diaper surface, flows backward in the large surface space as a passage, during which the urine is absorbed in the absorbent body 23 located on the back side. The conventional problem of diffusion block caused by the small surface space, accordingly, can be effectively prevented.

The shapes of the upper layer through section 50 and the lower layer thin section 64 in the second embodiment can also be upside down, though it is not shown in the drawings.

The others including the alternative versions are the same as in the first embodiment and the second embodiment, and the same explanations in the first embodiment and the second embodiment can also be applied to the third embodiment except that the shapes are upside down, and thus further explanations are intentionally omitted.

(Fourth Embodiment of Area for Forming Surface Depression)

In the first to third embodiments, the area for forming surface depression is on the absorbent body having the two-layer structure, but even if the area for forming surface depression of the present invention is provided on an absorbent body having a monolayer structure, as shown in FIG. 23 to FIG. 26, a disposable diaper having the same characteristics as above can also be obtained.

More specifically, in an embodiment shown in FIG. 23 to FIG. 26, at a center part of a crotch portion C2 of an absorbent body 23 having a monolayer structure in the width direction, an area for forming surface depression 231, which is an elongated first depression-formed part 231 extending in the front-back direction, and areas for forming surface depression 232, which are second depression-formed parts 232, 232 extending, in the width direction, from both sides of an intermediate position or a back side position of the first depression-formed part 231 in the front-back direction. The second depression-formed part 232 is a thin section which is thinner than the periphery thereof (which is not pierced in the thickness direction) while the first depression-formed part 231 is a through section piercing in the thickness direction.

In the disposable diaper having such absorbent body 23, when the disposable diaper is put between both legs and compressed in a width direction in a wearing state, depression 71, 72 are formed on the diaper surface as the areas for forming surface depression 231, 232 are deformed outward in order from the center in the width direction so as to be pushed out from the diaper. At that time, in the areas for forming surface depression 231 and 232, an area of the first depression-formed part 231 and the second depression-formed parts 232 is wider than an area of the first depression-formed part 231 by the width of the second depression-formed parts 232 and thus a wider depression 72 can be formed. Moreover, the stiffness of the wider depression 72 part is secured to a certain degree by the thin section, and thus maintainability of the shape and the depth of the depression 72, and further maintainability of the surface space become excellent. When urine is excreted, urine excreted in the depression 72 area and its front side, which is not absorbed and moves on the diaper surface, flows backward in the large surface space as a passage, during which the urine is absorbed in the absorbent body 23 located on the back side. A conventional problem of diffusion block caused by the small surface space, accordingly, can be effectively prevented.

Figure 27A:
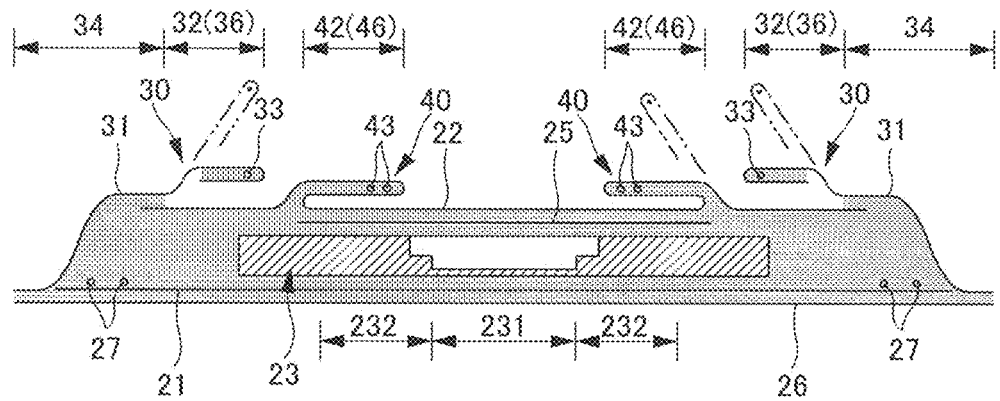
FIG. 27(a) is a cross-sectional view corresponding to a Z-Z cross-section in FIG. 23
Figure 27B:
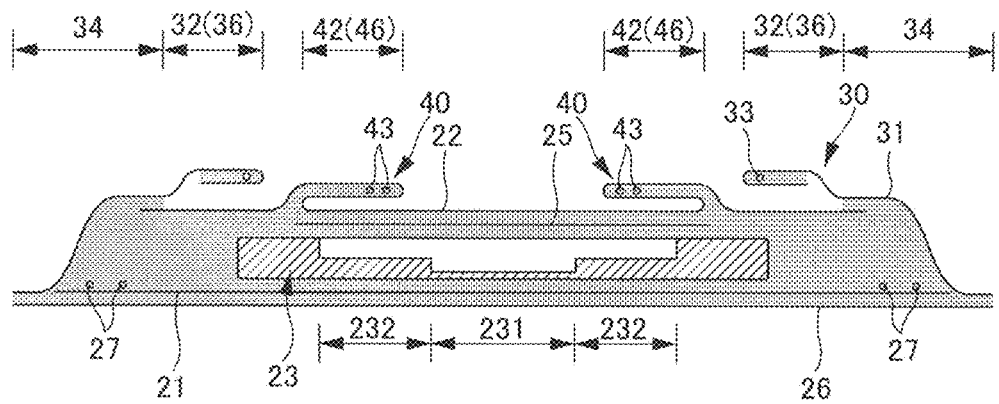
FIG. 27(b) is a view corresponding to an X-X cross-section in FIG. 23.
Figure 28:
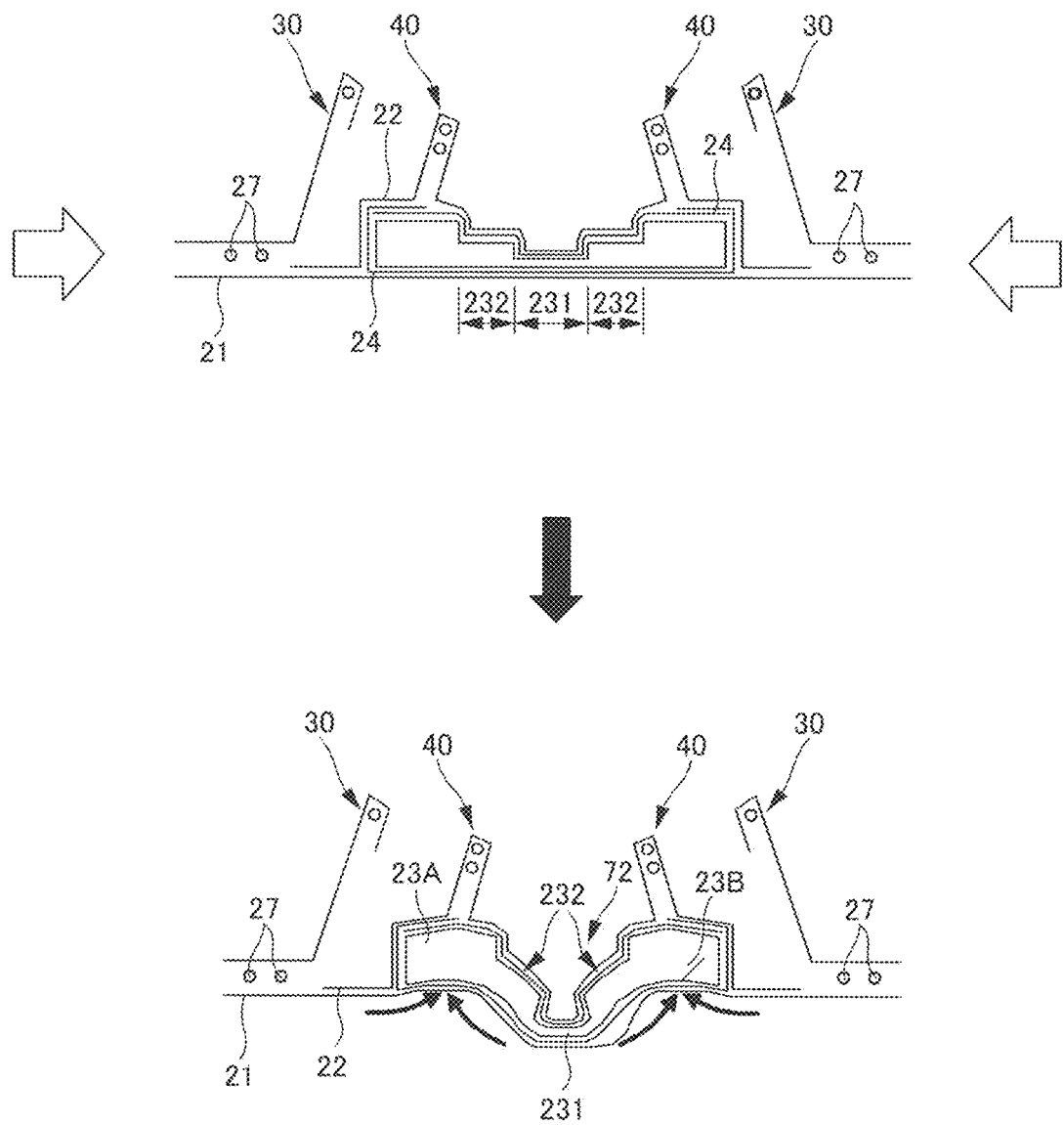
FIG. 28 is a schematic cross-sectional view showing change of a state before and after wearing.

It is also possible that the first depression-formed part 231 is not a through section but a thin section of which thickness is thinner than that of the second depression-formed part 232, as shown in FIG. 27 and FIG. 28. When the first depression-formed part 231 is a through section, high diffusibility of urine can be secured, but a passage, formed of the first depression-formed part 231, is easily deformed and is likely to be broken down. When the first depression-formed part 231 is formed into the thin section, accordingly, the passage formed of the first depression-formed part 231 can be easily maintained, and the diffusion of urine passing through the first depression-formed part 231 in the front-back direction can be promoted.

A thickness of the second depression-formed part 232 is not particularly limited, and it can be adjusted to about 10 to 50% of the thickness of parts excluding the areas for forming surface depression 231 and 232, and usually adjusted to about 1 to 5 mm. When the first depression-formed part 231 is the thin section, the thickness thereof is not particularly limited, and it can be adjusted to about 10 to 50% of the thickness of the second depression-formed part 232, and usually adjusted to about 1 to 5 mm. The thin section is not limited by a specific forming method, and for example, it can be formed by decreasing a basis weight thereof so as to be lower than that of the periphery thereof, or by compressing in the thickness direction (if necessary, heating can be added).

The first depression-formed part 231 may have the same size and shape as those of the lower layer through section 60 in the first embodiment. The shape of the first depression-formed part 231 may be a rectangular shape of which width is constant in the front-back direction as in the embodiments shown in the drawings, and can be appropriately changed to, for example, a shape of which width is changed in the front-back direction (for example, the width is increased gradually toward the back side), so long as it is the elongated shape. A size of the first depression-formed part 231 can be appropriately decided, and a length 231L in the front-back direction is preferably adjusted to about 180 to 210 mm, considering standard adults using this kind of disposable diaper. In addition, a width 231W of the first depression-formed part 231 can be appropriately decided, and in usual, it is preferably adjusted to about 20 to 40 mm, because not so large width is preferable in order to secure shape-maintaining property of depression 72. The multiple first depression-formed parts 231 may be provided at intervals in the width direction, as the lower layer through section 60 shown in FIG. 11 and FIG. 12.

It is also desirable that the first depression-formed part 231 is provided at a middle position of the absorbent body 23 in the front-back direction, i.e., the first depression-formed part 231 is disposed so that it does not extend to reach the front and back ends of the absorbent body 23, whereby the stiffness of the absorbent body 23 is secured as a whole.

The second depression-formed part 232 may have the same size and shape as those of the extending section 52 of the upper layer through section 50 in the first embodiment. A width 232W of the second depression-formed part 232 is desirably decided considering a size of the depression 72 (mainly a height of the wall) or a shape-maintaining property of the depression 72, and it is desirable that the total width of the width 231W of the first depression-formed part 231 and width 232W of the second depression-formed parts 232 is adjusted to about 1.5 to 2 times wider than the width 231W of the first depression-formed part 231, specifically adjusted to about 36 to 120 mm.

Positions of the second depression-formed parts 232 in the front-back direction can be appropriately decided. The second depression-formed part 232 may be formed by expanding sideward the first depression-formed part 231 at the back side position thereof as in the embodiments shown in the drawings, or the second depression-formed parts 232 may be formed by expanding sideward the first depression-formed part 231 at the intermediate position thereof in the front-back direction. The depression-formed part may be formed in which the first depression-formed part 231 is extended to the front side of the second depression-formed parts 232 and third depression-formed parts are further provided at the both sides in the width direction of the first depression-formed part 231 at the front side position thereof so as to exhibit front-back symmetry between the second depression-formed parts in the back side position and the third depression-formed parts in the front side position. In this case, a pair of the boat-shaped depressions face to each other through a narrow groove in a longitudinal direction (an almost sandglass-shaped depression is formed) in a wearing state, though it is not shown in drawings.

With respect to a shape of the second depression-formed part 232, a shape of the side edge thereof may be a bending line as in the embodiments shown in the drawings, or may be a curve line such as a circular arc. In the embodiments shown in the drawings, the shape is a trapezoid in which a boundary with the first depression-formed part 231 is a base line and the back edges are at right angles to the base line (a shape including the second depression-formed parts 232 and the first depression-formed part 231 between them is a pentagon) so that at least a part of the front side of the side edge of the second depression-formed part 232 is located further outside in the width direction toward the back side. The shape may be a trapezoid similar to the extending sections 52 shown in FIG. 10(a) (a shape including the extending sections 52 and the middle section 51 between them is a hexagon). A shape of the side edge of the second depression-formed part 232 may be, for example, a shape in which a part of the front side is located stepwise further outside in the width direction toward the back side, similar to the extending sections 52 shown in FIG. 13(a), a shape in which a part of the front side is located gradually further outside in the width direction toward the front side, similar to the extending sections 52 shown in FIG. 13(b), or a rectangular shape, similar to the extending sections 52 shown in FIG. 13(c).

In the embodiments shown in FIG. 23 to FIG. 26, high diffusibility of urine can be secured, because there is no absorbent body 23 in the site of the overlapped part with the first depression-formed part 231, however, the passage formed of the first depression-formed part 231 is easily deformed and is likely to be broken down. Accordingly, following the first embodiment, when a diffusion sheet 63 capable of promoting the diffusion of urine in the front-back direction is provided on the bottom of the first depression-formed part 231, the passage of the first depression-formed part 231 is easily maintained, and the diffusion of urine passing through the first depression-formed part 231 in the front-back direction can be promoted. Materials and alternative versions of the diffusion sheet 63 are the same as in the first embodiment, and thus the explanations thereof are intentionally omitted.

When three-dimensional gather 40 at the crotch portion is provided, as in the first embodiment, it is preferable that the second depression-formed part 232 is located between the non-standing parts 45 of the three-dimensional gather 40 at the crotch portion in the front-back direction (i.e., the position of the second depression-formed part 232 in the width direction is overlapped with the position of the non-standing part 45 of the three-dimensional gather 40 at the crotch portion in the width direction), because the contracting force owing to the resilient and elastic gather member 43 of the three-dimensional gather 40 at the crotch portion can be effectively acted on the second depression-formed part 232, the formation of the depression is promoted, and the shape-maintaining property of the depression is improved. However, the non-standing part 45 of the three-dimensional gather 40 at the crotch portion may also be located at the center side or the outside of the second depression-formed part 232 in the width direction.

The position of the base end of the extending section 42 in the width direction in the three-dimensional gather 40 at the crotch portion is desirably separated sideward from the second depression-formed part 232 as shown in the embodiments shown in the drawings, but it can be aligned with the side edge of the extending section 52, or can be located within the extending section 52. In addition, it is most preferable that a position of a front edge of the extending section 42 in the width direction in the three-dimensional gather 40 at the crotch portion is located on a part passing through the second depression-formed part 232 in the developed state. Due to these locations, the second depression-formed part 232 can be easily folded to the underside along the side edge thereof so that the depression 72 can be formed and maintained reliably. The others are the same as the three-dimensional gather 40 at the crotch portion in the first embodiment, and thus the explanations thereof are intentionally omitted.

(Others)

In the first to the fourth embodiments as described above, the absorbent body 23 has the two-layer structure or the monolayer structure, but it may have a three- or more-layer structure. The areas for forming surface depression 231 and 232 can be formed from any one or combined layers of the through section, the thin section (which is compressed or has a low basis weight), and the absorbent body 23, within the scope of the present invention. The present invention encompasses the embodiment in which only the thin section is provided in the absorbent body 23 having a multi-layer structure without any through section, as the fourth embodiment.

It is enough that the areas for forming surface depression 231 and 232 are provided in a range of the crotch portion C2 in the front-back direction, and it is particularly desirable that the first depression-formed part 231 extends from the front to the back side of the scrotum-disposed region C1, and the second depression-formed parts 232 extend backward from the intermediate position or back side position of the scrotum-disposed region C1 in the front-back direction. It is also preferable that, as in the embodiments shown in the drawings, when the narrower part 23*n* with small width is provided at the middle of the absorbent body 23 in the front-back direction, the first depression-formed part 231 and the second depression-formed parts 232 extend up to the area in which the width of the narrower part 23*n* is gradually increased toward the back side in the front-back direction, or the area behind thereof.

<Explanations of Terms in Specification>

The following terms in the specification have the following meanings unless otherwise noted.

The "basis weight" is measured as follows: A specimen having a size of 100 mm×100 mm (±2 mm) is cut from a sample using a roll cutter. A weight of the specimen is measured, and a weight per square meter is calculated, which is defined as the basis weight.

The "thickness" is measured using a thickness measuring apparatus manufactured by Ozaki Mfg. Co., Ltd. (PEACOCK, Dial Thickness Gauge Large Size, Model J-B (measurement range: from 0 to 35 mm) or Model K-4 (a measurement range: from 0 to 50 mm)) in which the sample and the measuring apparatus are horizontally set.

INDUSTRIAL APPLICABILITY

The present invention can be utilized in all disposable diapers of pad-type, pants-type, and tape-type diapers.

REFERENCE SIGNS LIST

B2 Back side part
C1 Scrotum-disposed region
C2 Crotch portion
F2 Front side part
21 Liquid-impermeable sheet
22 Top sheet
23 Absorbent body
23A Upper layer absorbent body
23B Lower layer absorbent body
23*n* Narrower part
23*w* Monolayer structure part
25 Interlayer sheet
26 Outer sheet
30 Three-dimensional gather at the side part
31 Three-dimensional gather sheet at the side part
33 Resilient and elastic gather member
40 Three-dimensional gather at the crotch portion
42 Extending section
43 Resilient and elastic gather member
50 Upper layer through section
51 Middle section
52 Extending section
60 Lower layer through section
63 Diffusion sheet
64 Lower layer thin section
231 First depression-formed part
232 Second depression-formed part
231, 232 Area for forming surface depression.

The invention claimed is:

1. A disposable diaper comprising a crotch portion, a back side part extending backward from the crotch portion, and an absorbent body extending from the crotch portion to the back side part for absorbing urine, wherein the absorbent body contains a lower layer absorbent body and an upper layer absorbent body provided on the lower layer absorbent body, the lower layer absorbent body has, at least at center of the crotch portion in a width direction, an elongated lower layer through section piercing in a thickness direction and extending in a front-back direction, the upper layer absorbent body has an upper layer through section piercing in the thickness direction at least within a range corresponding to the lower layer through section in the front-back direction, and the upper layer through section has an elongated middle section extending in the front-back direction so as to be located above the lower layer through section, and extending sections extending in the width direction, from both sides of an intermediate position or a back side position of the middle section in the front-back direction, three-dimensional gathers at the crotch portion extend at both sides of a diaper surface in the width direction, each three-dimensional gather has a projecting portion, which projects from a lateral side of the upper layer through section and which extends in the front-back direction, the projecting portion contains non-standing parts, which are fixed in a fallen state and which are positioned in a front side and in a back side of the projecting portion respectively, and a standing part, which is not fixed, which is disposed between the non-standing parts, and which has a resilient and elastic gather member fixed in a stretched state in the front-back direction, and the extending section is located between the non-standing parts of the three-dimensional gather at the crotch portion in the front-back direction and overlaps the non-standing parts in the width direction.

2. The disposable diaper according to claim 1, wherein the middle section of the upper layer through section extends up to a front end of the upper layer absorbent body, and opens at the front end of the upper layer absorbent body, and the front end of the upper layer absorbent body is located at a same position as or a back side position of a front end of the lower layer through section.

3. The disposable diaper according to claim 1, wherein the lower layer through section is provided at an intermediate position of the lower layer absorbent body in the front-back direction.

4. The disposable diaper according to claim 1, which contains a diffusion sheet, which promotes urine diffusion in the front-back direction, on a bottom of the lower layer through section.

5. The disposable diaper according to claim 1, wherein a side edge of the extending section has a shape in which at least a part of the front side thereof is located further outside in the width direction toward the back side.

6. The disposable diaper according to claim 5, wherein the extending section has a trapezoid shape whose base line is a boundary with the middle section.

* * * * *